(12) United States Patent
Nilsson et al.

(10) Patent No.: US 10,978,204 B2
(45) Date of Patent: Apr. 13, 2021

(54) BAR-TYPE PARAMETER ADJUSTMENT ELEMENTS

(71) Applicant: GAMBRO LUNDIA AB, Lund (SE)

(72) Inventors: Roger Nilsson, Hoor (SE); Bendik Torvin, Schaanwald (LI)

(73) Assignee: Gambro Lundia AB, Lund (SE)

(*) Notice: Subject to any disclaimer, the term of this patent is extended or adjusted under 35 U.S.C. 154(b) by 208 days.

(21) Appl. No.: 16/090,418

(22) PCT Filed: Mar. 29, 2017

(86) PCT No.: PCT/EP2017/057352
§ 371 (c)(1),
(2) Date: Oct. 1, 2018

(87) PCT Pub. No.: WO2017/167773
PCT Pub. Date: Oct. 5, 2017

(65) Prior Publication Data
US 2019/0115103 A1   Apr. 18, 2019

(30) Foreign Application Priority Data
Apr. 1, 2016  (SE) .................................. 1650432-6

(51) Int. Cl.
*G06F 3/048*    (2013.01)
*G16H 40/63*    (2018.01)
(Continued)

(52) U.S. Cl.
CPC .......... *G16H 40/63* (2018.01); *A61M 1/1621* (2014.02); *G06F 3/04847* (2013.01); *G06F 3/04883* (2013.01)

(58) Field of Classification Search
CPC ................................................ G06F 2200/163
See application file for complete search history.

(56) References Cited

U.S. PATENT DOCUMENTS

| 5,371,846 A | 12/1994 | Bates |
| 5,609,770 A | 3/1997 | Zimmerman |

(Continued)

FOREIGN PATENT DOCUMENTS

| DE | 19742633 | 4/1999 |
| DE | 10013666 | 10/2011 |

(Continued)

OTHER PUBLICATIONS

PCT Search Report and Written Opinion for PCT/EP2017/057353 dated Jul. 13, 2017 (22 pages).

(Continued)

*Primary Examiner* — Di Xiao
(74) *Attorney, Agent, or Firm* — Mueting Raasch Group

(57) ABSTRACT

Graphical user interfaces for use with extracorporeal blood treatment systems may include one or more bar-type parameter adjustment elements. The bar-type parameter adjustment elements may be used to ascertain and adjust one or more parameters related to one or more processes performed by the extracorporeal blood treatment systems. The bar-type parameter adjustment element may be scaled such that midpoint of the bar-type parameter adjustment element is representative of a reference value.

22 Claims, 15 Drawing Sheets

(51) Int. Cl.
*G06F 3/0484* (2013.01)
*A61M 1/16* (2006.01)
*G06F 3/0488* (2013.01)

(56) References Cited

U.S. PATENT DOCUMENTS

| | | | |
|---|---|---|---|
| 6,024,089 A | 2/2000 | Wallace | |
| 7,735,020 B2 * | 6/2010 | Chaudhri | G06F 3/04847 715/784 |
| 2002/0033850 A1 | 3/2002 | Bates | |
| 2005/0045540 A1 | 3/2005 | Connell | |
| 2006/0136836 A1 | 6/2006 | Clee | |
| 2006/0162727 A1 | 7/2006 | Biondi | |
| 2006/0258985 A1 | 11/2006 | Russell | |
| 2008/0024459 A1 | 1/2008 | Poupyrev | |
| 2008/0034323 A1 | 2/2008 | Blomquist | |
| 2009/0061947 A1 | 3/2009 | Park | |
| 2010/0069153 A1 | 3/2010 | Takahashi | |
| 2011/0004841 A1 * | 1/2011 | Gildred | H04N 1/0044 715/780 |
| 2011/0080367 A1 | 4/2011 | Marchand | |
| 2011/0152739 A1 | 6/2011 | Roncadi | |
| 2012/0238851 A1 | 9/2012 | Kamen | |
| 2012/0323212 A1 | 12/2012 | Murphy | |
| 2013/0061152 A1 | 3/2013 | Dolgos | |
| 2013/0112202 A1 | 5/2013 | Fogelbrink | |
| 2013/0190717 A1 | 7/2013 | Dollar | |
| 2013/0254717 A1 | 9/2013 | Al-Ali | |
| 2013/0293570 A1 | 11/2013 | Dolgos | |
| 2013/0298062 A1 * | 11/2013 | Dolgos | G06F 19/32 715/771 |
| 2014/0099235 A1 | 4/2014 | Ellingboe | |
| 2015/0193585 A1 | 7/2015 | Sunna | |
| 2015/0355790 A1 | 12/2015 | O'Mahony | |
| 2018/0321843 A1 | 11/2018 | Giannotti | |

FOREIGN PATENT DOCUMENTS

| | | |
|---|---|---|
| WO | WO 94/11093 | 5/1994 |
| WO | WO 2011/014704 | 2/2011 |
| WO | WO 2014/033119 | 3/2014 |
| WO | WO 2015/033288 | 3/2015 |
| WO | WO 2015/153253 | 10/2015 |
| WO | WO 2015/153254 | 10/2015 |

OTHER PUBLICATIONS

PCT Search Report and Written Opinion for PCT/EP2017/057352 dated May 19, 2017 (13 pages).

* cited by examiner

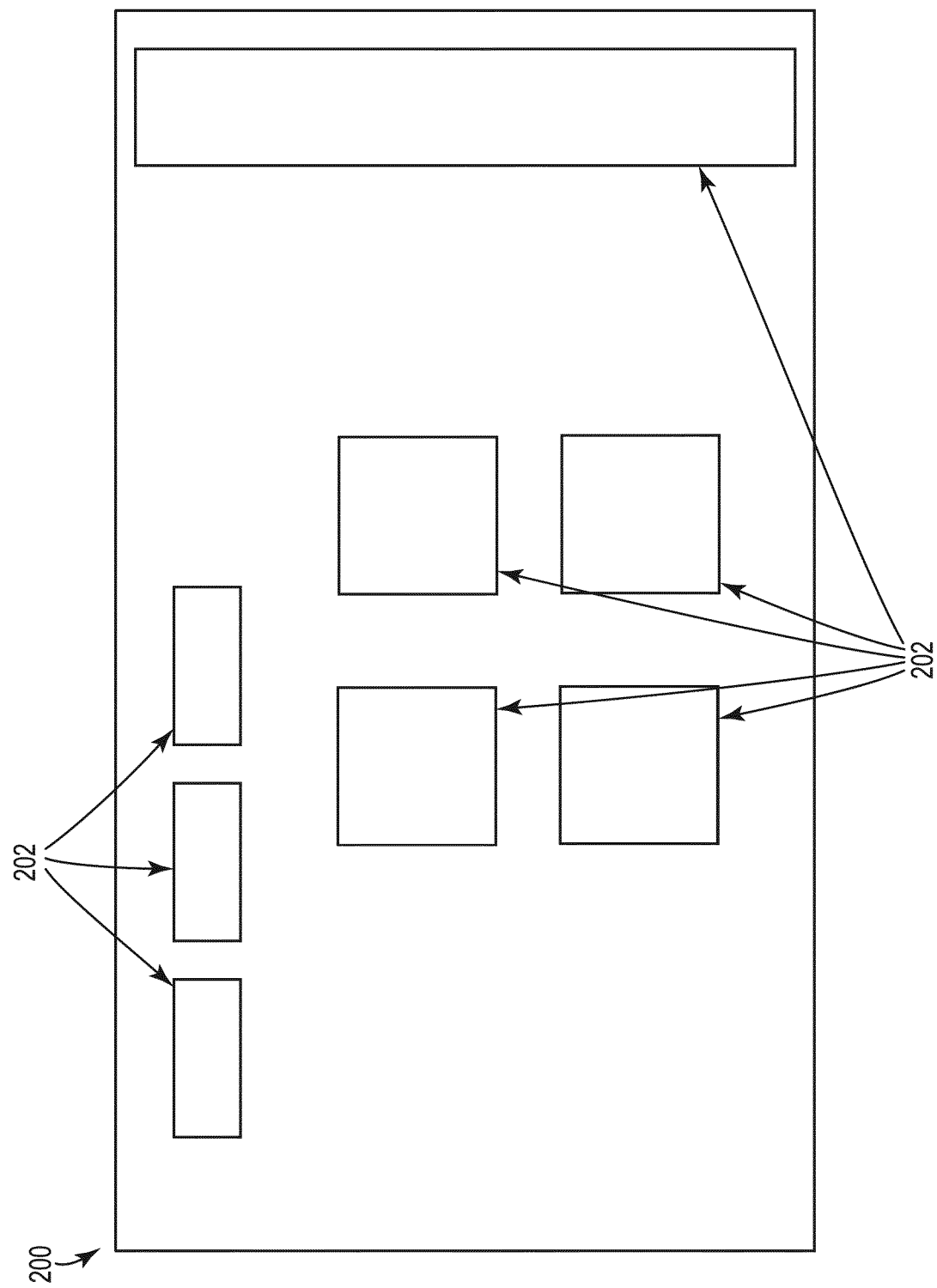

BAR-TYPE PARAMETER ADJUSTMENT ELEMENTS

This application is a U.S. National Stage Application of International Application No. PCT/EP2017/057352, filed 2017 Mar. 29 and published in English on 2017 Oct. 5 as International Publication No. WO 2017/167773 A1, which claims the benefit of priority under 35 U.S.C. § 119(a) of Swedish Patent Application No. 1650432-6 filed 2016 Apr. 1, each of which are incorporated herein by reference in their entireties.

The disclosure herein relates to medical treatment apparatus. More particularly, the disclosure relates to systems and methods for use in providing graphical user interfaces related to medical treatment apparatus such as extracorporeal blood treatment apparatus.

Medical treatment apparatus often includes a graphical user interface depicted on a display. A user may use the graphical user interface to, among other things, configure and setup a treatment, monitor and perform a treatment, and perform various post-treatment processes. The graphical user interface for treatment apparatus may include a plurality of different graphical elements, graphical regions, and graphical areas configured for performing the functionality associated with the treatment apparatus.

Medical treatment apparatus may be configured to perform extracorporeal blood treatment. Extracorporeal blood treatment may refer to taking blood from a patient, treating the blood outside the patient, and returning the treated blood to the patient. Extracorporeal blood treatment is typically used to extract undesirable matter or molecules from the patient's blood, and/or to add beneficial matter or molecules to the blood. Extracorporeal blood treatment may be used with patients incapable of effectively eliminating such undesirable matter from their blood, for example, in the case of a patient who is suffering from temporary or permanent kidney failure. These and other patients may, for instance, undergo extracorporeal blood treatment to add to or to eliminate matter from their blood, to maintain an acid-base balance, and/or to eliminate excess body fluids.

SUMMARY

Medical treatment apparatus may include graphical user interfaces that make the presentation and adjustments of settings, or parameters, related to medical treatments overly complex and number-based such that the graphical user interfaces intimidate users and/or operators. For example, such graphical user interfaces may tend to be crowded with numbers related to medical treatments. Further, it may be difficult, especially for novices, to obtain, or get, a simple overview of the meaning of many displayed numbers, in particular, when setting up a new treatment. In addition, the displayed parameters that may be adjusted are often scattered in many different places over the graphical user interfaces, which, e.g., may require skill and patience to locate.

Further, medical treatment apparatus may include graphical user interfaces that display values of parameters as numbers. Upon viewing, the displayed numbers may have to be processed by the human brain to have meaning. Further, the displayed numbers themselves may have relative meaning. For example, the number "40" can be both very high and very low depending on context, e.g., depending on which type of parameter it represents. For example, the number "40' when representing a blood flow value may be very low while the same number "40" when representing temperature may be very high in the context of extracorporeal blood treatments. Instead, sliders, or number-scales, may be used to graphically display values of parameters and may be located close to one another. Deciphering the relative values of parameters represented by the sliders may be easier and use a lower amount of brain processing power, which may result in reduced error and stress.

The exemplary bar-type adjustment elements described herein may overcome usability problems and may reduce sources of error by offering a way to present and adjust number/value-based parameters, or settings, related to a medical treatment on a medical treatment apparatus. By presenting input values and read-out values on vertical sliders, e.g., as a "handle," placed on a vertical sliding track (e.g., similar to a track on an "equalizer"), users and/or operators may automatically and intuitively visualize the current, or present, parameter value and the parameter's upper and lower limits. Further, as the upper end of the slider is a maximum and the lower is the minimum, the middle may automatically represent the average or median value for the parameter. The middle may automatically represent a reference value, which may be based on clinic presets, the patient's previous treatment average, and/or a prescription.

Further, the exemplary bar-type adjustment elements may be presented side-by-side to, e.g., give users/operators an extraordinary overview and instinctive "feeling" of the current status of multiple parameters/settings. In the context of dialysis treatment, the exemplary bar-type parameter adjustment elements may be an effective way to create clarity, overview, and understanding of what was previously an intimidating display of a plurality of numbers related to the dialysis treatment.

The effect of the "equalizer design" of the exemplary bar-type parameter adjustment elements may be that the operator may instantly see if an input parameter or read-out parameter related to a medical treatment (e.g., an extracorporeal blood treatment) is higher or lower than normal when the indicator element, or "handle," is not in the middle (e.g., on the midpoint line). Thus, understanding the meaning of the parameter-values related to the medical treatment on the screen may then become easier. Further, gathering many parameters, or settings, related to a medical treatment together side-by-side may also make it easy to see any deviant values at a glance, even for many parameters at the same time. Still further, the exemplary bar-type parameter adjustment elements may increase the sense of control, may reduce stress, may reduce confusion, and may reduce risk of error because high and low limits may be immediately detectable and apparent. Also, using indicator elements, or sliders, as an input method may also be more pleasant, faster, and less error-prone than using a keypad. It may be described that the exemplary bar-type parameter adjustment elements translate to a better, more efficient working environment for the operator, and thereby, a safer and better treatment experience for the patient.

Users may desire processes and methods of confirming values related to a medical treatment set using a bar-type parameter adjustment element or "sliders." Further, users may also desire graphical user interfaces where previous values are still available to provide users the possibility to change their mind and not follow through in updating a value. Still further, value confirmation may be performed by selecting, or clicking, confirmation regions or "tick boxes," which may require users to move their fingers to an additional location. The disclosure herein may describe systems, methods, and interfaces that do not require users to lift their fingers after value selection, and instead, may make it possible to perform "undo" and "confirm" functionality with a single selection, or contact, of the touchscreen.

The present disclosure describes systems and methods that use, or utilize, graphical user interfaces that depict one or more graphical elements that may be used to adjust one or more parameters or values related to one or more medical treatments and associated with medical treatment apparatus. More specifically, the one or more graphical elements may include bar-type parameter adjustment elements, or "sliders," associated with various parameters related to one or more processes features of one or more medical treatments performable by the medical treatment apparatus. Each bar-type parameter adjustment element may include a bar element and an indicator, or adjustment, element located along the bar element to indicate the present value of the parameter associated therewith. Further, a user may adjust the parameter associated with the bar-type parameter adjustment element in various ways. For example, a user may select (e.g., tap, if using a touchscreen) above the indicator element or below the indicator element along the bar element to incrementally increase or decrease, respectively, the associated parameter related to the medical treatment by a preset, or selected, incremental value (e.g., a set amount). Further, for example, a user may select and drag the indicator element upwardly or downwardly along the bar element to increase or decrease, respectively, the associated parameter related to the medical treatment.

Each bar-type parameter adjustment element may be described as a "controller" for the associated parameter related to a medical treatment that may be used to control, or adjust, the associated parameter related to the medical treatment. Further, each bar-type parameter adjustment element may be described as providing control of events or conditions (e.g., parameters) that are internal to the technical medical treatment system or apparatus. Still further, each bar-type parameter adjustment element may be described as a way, or process, by which the medical treatment system, or apparatus, prompts a user to interact with the system, or apparatus, so as to in a way to enable proper functionality of the system to perform one or more medical treatment such as, e.g., extracorporeal blood treatments. Yet still further, each of the parameters related to the medical treatment that are associated with the exemplary bar-type adjustment elements may be described as presenting cognitive information constituting, or representing, one or more states, such as operational states, of the medical system. And still further, the bar-type parameter adjustment elements may be described as providing technical information intrinsically tied to, or associated with, the medical system and the medical treatments performable by the medical system and as providing control, or adjustment of the technical information to control, or adjust, actual functional characteristics of the medical system and/or medical treatments performable thereby.

One exemplary extracorporeal blood treatment system may include extracorporeal blood treatment apparatus comprising one or more pumps, one or more sensors, and one or more disposable elements for use in performing an extracorporeal blood treatment, a display, and a processor operatively coupled to the extracorporeal blood treatment apparatus and the display. The display may include a graphical user interface configured to depict a parameter adjustment region corresponding to a plurality of parameters related to the extracorporeal blood treatment performable using the extracorporeal blood treatment apparatus. The processor may be configured to provide a plurality of parameters related to the extracorporeal blood treatment performable using the extracorporeal blood treatment apparatus and a plurality of reference values. Each of the plurality of reference values may be associated with a different parameter of the plurality of parameters, and each of the plurality of reference values may represent a selected prescription value, a preset default value, or a saved value for a patient for each associated parameter of the plurality of parameters. The processor may be further configured to display the parameter adjustment region on the graphical user interface. The parameter adjustment region may include a plurality of bar-type parameter adjustment elements displayed simultaneously, and each of the plurality of bar-type parameter adjustment elements may be associated with and configured to adjust a different parameter of the plurality of parameters. Each of the plurality of bar-type parameter adjustment elements may include a bar element extending from a first end representative of a lower value for the associated parameter to a second end representative of an upper value for the associated parameter and scaled such that a midpoint between the first end and the second end is representative of the reference value for the associated parameter, and an indicator element located along the bar element between the first end and the second end indicative of a present value of the associated parameter. The plurality of bar-type parameter adjustment elements may be aligned with respect to each other such the bar elements of the plurality of bar-type parameter adjustment elements are parallel each other. The processor may be further configured to change a parameter of the plurality of parameters related to the extracorporeal blood treatment performable using the extracorporeal blood treatment apparatus in response to a user using a bar-type parameter adjustment of the plurality of bar-type parameter adjustment elements associated with the parameter to adjust the parameter. In other words, the processor may be further configured to allow a user to adjust the plurality of parameters using the plurality of bar-type parameter adjustment elements.

One exemplary method for an extracorporeal blood treatment system may include providing extracorporeal blood treatment apparatus including one or more pumps, one or more sensors, and one or more disposable elements for use in performing an extracorporeal blood treatment, displaying a parameter adjustment region corresponding to a plurality of parameters related to the extracorporeal blood treatment performable using the extracorporeal blood treatment apparatus on a graphical user interface on a display, and providing a plurality of parameters related to the extracorporeal blood treatment performable using the extracorporeal blood treatment apparatus and a reference value for each parameter of the plurality of parameters. The reference value may represent a selected prescription value, a preset default value, or a saved value for a patient for each parameter of the plurality of parameters. The method may further include displaying the parameter adjustment region on the graphical user interface. The parameter adjustment region may include a plurality of bar-type parameter adjustment elements displayed simultaneously, and each of the plurality of bar-type parameter adjustment elements may be associated with and configured to adjust a different parameter of the plurality of parameters related the extracorporeal blood treatment. Each of the plurality of bar-type parameter adjustment elements may include a bar element extending from a first end representative of a lower value for the associated parameter to a second end representative of an upper value for the associated parameter and scaled such that a midpoint between the first end and the second end is representative of the reference value for the associated parameter, and an indicator element located along the bar element between the first end and the second end indicative of a present value of the associated parameter. The plurality of bar-type parameter adjustment elements may be aligned with respect to each other such the bar elements of the plurality of bar-type parameter adjustment elements are parallel each other. The method may further include changing a parameter of the plurality of parameters related to the extracorporeal blood treatment performable using the extracorporeal blood treatment apparatus in response to a user using a bar-type parameter adjustment element of the plurality of bar-type parameter adjustment elements associated with the parameter to adjust the parameter. In other words, the method may further include allowing a user to adjust the plurality of parameters using the plurality of bar-type parameter adjustment elements.

In one or more embodiments, changing a parameter of the plurality of parameters related to the extracorporeal blood treatment performable using the extracorporeal blood treatment apparatus in response to a user using a bar-type parameter adjustment element associated with the parameter to adjust the parameter may include changing the parameter in response to a user tapping an area between the indicator element and the first end or an area between the indicator element and the second end along the bar element of each bar-type parameter adjustment element to decrease or increase, respectively, the associated parameter by a step percentage of the upper value for the parameter. In at least one embodiment, the step percentage may be less than or equal to about 10 percent of the upper value for the parameter.

In one or more embodiments, changing a parameter of the plurality of parameters related to the extracorporeal blood treatment performable using the extracorporeal blood treatment apparatus in response to a user using a bar-type parameter adjustment element associated with the parameter to adjust the parameter may include allowing a user to select the indicator element and drag the indicator element along the bar element towards the first end or the second end of each bar-type parameter adjustment element to decrease or increase, respectively, the associated parameter. In other words, allowing a user to adjust the plurality of parameters using the plurality of bar-type parameter adjustment elements may include allowing a user to select the indicator element and drag the indicator element along the bar element towards the first end or the second end of each bar-type parameter adjustment element to decrease or increase, respectively, the associated parameter. In at least one embodiment, the processor may be further configured to execute or the method may further include changing the associated parameter to a value associated with a new position of the indicator element along the bar element in response to the user maintaining selection of the indicator element at the new position for a confirmation time period.

In one or more embodiments, the indicator element may be configurable in a locked state and in an unlocked state. The indicator element may be unmovable along the bar element by selecting and dragging the indicator element when in the locked state, and the indicator element may be movable along the bar element by selecting and dragging the indicator element when in the unlocked state. Further, the processor may be further configured to execute or the method may further include configuring the indicator element in the locked state when the indicator element is not selected by a user, and configuring the indicator element in an unlocked stated in response to selection and maintenance of the selection of the indicator element by a user for a unlock time period. In other words, a user may be allowed to select and maintain selection of the indicator element for a unlock time period to configure the indicator element into the unlocked state. In at least one embodiment, the unlock time period may be less than or equal to 250 milliseconds.

In one or more embodiments, each of the plurality of bar-type parameter adjustment elements further may include an alphanumeric depiction of the associated parameter, and the processor may be further configured to execute or the method may further include: initiating an adjustment of a parameter of the plurality of parameters in response to selection of the alphanumeric depiction of the bar-type parameter adjustment element of the plurality of bar-type parameter adjustment elements associated with the parameter (e.g., in other words, allowing a user to select the alphanumeric depiction of the plurality of bar-type parameter adjustment elements to initiate an adjustment of the associated parameters), and displaying an alphanumeric parameter entry region in response to selection of the alphanumeric depiction to allow the user to change, or adjust, the associated parameter.

In one or more embodiments, the processor may be further configured to execute or the method may further include displaying on the graphical user interface one or more blood process feature, or treatment, graphical elements corresponding to one or more processes of the extracorporeal blood treatment system, and allowing a user to select a blood process feature, or treatment, graphical element of the one or more blood process feature, or treatment, graphical elements to display the parameter adjustment region.

In one or more embodiments, the plurality of parameters of the parameter adjustment region may be related to one of priming, ultrafiltration, and dialysis fluid. Further, the plurality of parameters of the parameter adjustment region may be related to a prescription for an extracorporeal blood treatment. In one or more embodiments, the display may include a touchscreen.

In one or more embodiments, the exemplary systems and methods may include a confirmation step and may also include undo functionality, which may use a single selection (e.g., touch, press, etc.) on a touchscreen. The disclosure herein may be described as being capable of reducing accidental changes of the indicator element, or slider handle, position while at the same time minimizing a user's effort to quickly adjust the indicator element, or slider handle, to a confirmed value.

The above summary of the present disclosure is not intended to describe each embodiment or every implementation thereof. Advantages, together with a more complete understanding of the present disclosure, will become apparent and appreciated by referring to the following detailed description and claims taken in conjunction with the accompanying drawings.

BRIEF DESCRIPTION OF THE DRAWING

FIGS. 3A-3B depict an exemplary graphical user interface for use in adjusting one or more parameters using an extracorporeal blood treatment system such as, for example, shown generally in FIGS. 1-2.

DETAILED DESCRIPTION OF EXEMPLARY EMBODIMENTS

Figure 1:
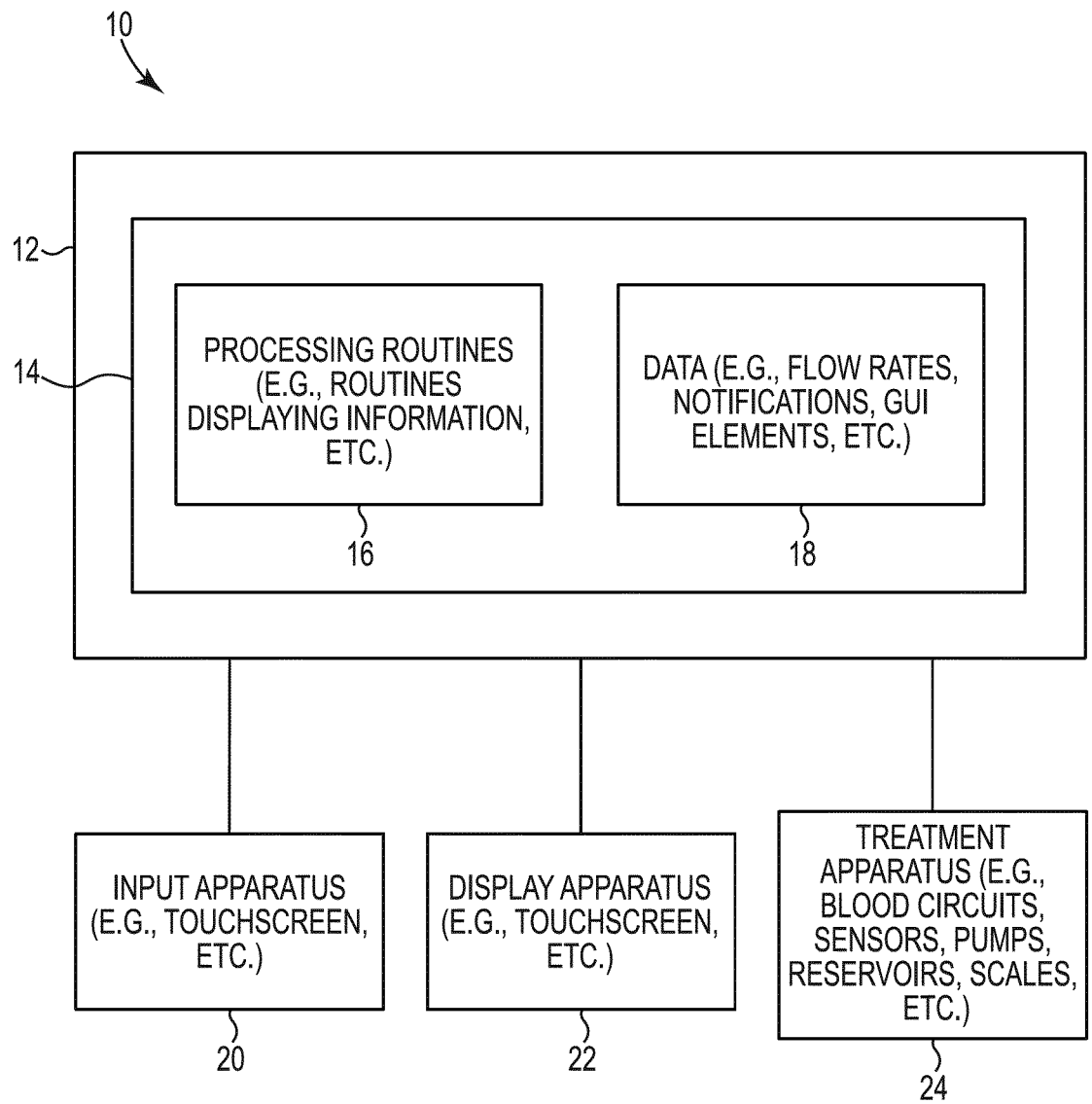
FIG. 1 is a block diagram of an exemplary medical treatment system including input apparatus, display apparatus, and treatment apparatus that may utilize the graphical user interfaces and methods described herein.

In the following detailed description of illustrative embodiments, reference is made to the accompanying figures of the drawing, which form a part hereof, and in which are shown, by way of illustration, specific embodiments that may be practiced. It is to be understood that other embodiments may be utilized and structural changes may be made without departing from (e.g., still falling within) the scope of the disclosure presented hereby.

Exemplary graphical user interface systems and methods for use with medical treatment apparatus such as, e.g., extracorporeal blood treatment apparatus, shall be described with reference to FIGS. 1-9. It will be apparent to one skilled in the art that elements or processes from one embodiment may be used in combination with elements or processes of the other embodiments, and that the possible embodiments of such graphical user interface systems and methods using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

The exemplary systems and/or methods may provide, or include, graphical user interfaces (e.g., user-interactable graphical user interfaces, graphical user interfaces depicted on single-touch or multi-touch touchscreens, etc.) that include, or depict, a plurality of graphical elements, graphical regions, and graphical areas configured to allow a user to adjust one or more parameters, or values, with respect to one or more processes (e.g., one or more processes of an extracorporeal blood treatment system, etc.). In particular, the graphical user interfaces may include a parameter adjustment region used to adjust one or more parameters. The parameter adjustment region may include one or more bar-type parameter adjustment elements configured to allow a user to visualize, or ascertain, the present value for the parameters associated therewith and to adjust such parameters.

An exemplary extracorporeal blood treatment system 10 depicted in FIG. 1 may be used to execute, or perform, the exemplary methods and/or processes described herein. In at least one embodiment, the system 10 may be a machine for the extracorporeal treatment of blood. The system 10 could, for example, alternatively be a blood processing device or a blood component preparation device or other medical apparatus for fluid delivery/collection.

As shown, the exemplary extracorporeal blood treatment system 10 includes computing apparatus 12. The computing apparatus 12 may be configured to receive input from input apparatus 20 and transmit output to display apparatus 22. Further, the computing apparatus 12 may include data storage 14. Data storage 14 may allow for access to processing programs or routines 16 and one or more other types of data 18 (e.g., graphical regions, graphical elements, graphical areas, graphical animations, parameters, metrics, variables, images, values, limits, text strings, macros, etc.) that may be employed to perform, or carry out, exemplary methods and/or processes (e.g., displaying graphical user interfaces, allowing user interaction with graphical user interfaces, interpreting touch gestures on a touchscreen (e.g., swipes, drags, press-and-hold, touches, presses, etc.), displaying graphical elements, displaying graphs, displaying textual elements, displaying textual values, displaying status information, issuing alarms, running a treatment, determining problems with a treatment, exchanging/changing reservoirs, notifying operators/users of problems, etc.) for use in performing extracorporeal blood treatments. The computing apparatus 12 may be operatively coupled to the input apparatus 20 and the display apparatus 22 to, e.g., transmit data to and from each of the input apparatus 20 and the display apparatus 22. For example, the computing apparatus 12 may be operatively coupled to each of the input apparatus 20 and the display apparatus 22 using, e.g., analog electrical connections, digital electrical connections, wireless connections, bus-based connections, etc. As described further herein, an operator may provide input to the input apparatus 20 to manipulate, or modify, one or more graphical elements, graphical regions, and graphical areas displayed on the display apparatus 22 to, e.g., initiate one or more actions and/or processes related to the extracorporeal blood treatment system, indicate one or more actions and/or statuses related to one or more processes of the extracorporeal blood treatment system, etc.

Further, various devices and apparatus may be operatively coupled to the computing apparatus 12 to be used with the computing apparatus 12 to perform one or more extracorporeal procedures/treatments as well as the functionality, methods, and/or logic described herein. As shown, the system 10 may include input apparatus 20, display apparatus 22, and treatment apparatus 24 operatively coupled to the computing apparatus 12 (e.g., such that the computing apparatus 12 may be configured to use information, or data, from the apparatus 20, 22, 24 and provide information, or data, to the apparatus 20, 22, 24). The input apparatus 20 may include any apparatus capable of providing input to the computing apparatus 12 to perform the functionality, methods, and/or logic described herein.

For example, the input apparatus 20 may include a touchscreen (e.g., capacitive touchscreen, a resistive touchscreen, a multi-touch touchscreen, etc.), a mouse, a keyboard, a trackball, etc. A touchscreen may overlay the display apparatus 22 such that, e.g., an operator may use the touchscreen to interact (e.g., by touch) with a graphical user interface displayed on the display apparatus 22. For example, the input apparatus 20 may allow an operator to interact with a graphical user interface including an operation region containing, or depicting, graphical elements, graphical regions, and graphical areas associated with and representative of (or corresponding to) one or more features or processes of the extracorporeal blood treatment system when used in conjunction with the display apparatus 22 (e.g., displaying the graphical user interface). Further, more specifically, the input apparatus 20 may allow an operator to interact with a graphical user interface including various bar-type parameter adjustment elements associated with various adjustable parameters when used in conjunction with the display apparatus 22 (e.g., displaying the graphical user interface).

The display apparatus 22 may include any apparatus capable of displaying information to an operator, such as a graphical user interface, etc., to perform the functionality, methods, and/or logic described herein. For example, the display apparatus 22 may include a liquid crystal display, an organic light-emitting diode screen, a touchscreen, a cathode ray tube display, etc. As described further herein, the display apparatus 22 may be configured to display a graphical user interface that includes one or more graphical regions, graphical elements, and graphical areas.

For example, the graphical user interface displayed by the display apparatus 22 may include, or display, an operation region that may include multiple graphical regions, graphical areas, and graphical elements related to the extracorporeal blood treatment system. Such graphical regions, graphical areas, and graphical elements may include a parameter adjustment region used to ascertain and/or adjust one or more parameters associated with one or more processes of the extracorporeal blood treatment system.

As used herein, a "region" of a graphical user interface may be defined as a portion of the graphical user interface within which information may be displayed or functionality may be performed. Regions may exist within other regions, which may be displayed separately or simultaneously. For example, smaller regions may be located within larger regions, regions may be located side-by-side, etc. Additionally, as used herein, an "area" of a graphical user interface may be defined as a portion of the graphical user interface located within a region that is smaller than the region within which the area is located. Still further, as used herein, an "element" of a graphical user interface may be defined as a component of the graphical user interface that may be located within, or adjacent to, a region, an area, or another element. In one or more embodiments, an "element" of a graphical user interface may include a perimeter, or border, defining the outer edge, or boundary, of the element. In one or more embodiments, an "element" of a graphical user interface is a defined, finite portion, item, and/or section of a graphical user interface.

The processing programs or routines 16 may include programs or routines for performing computational mathematics, touchscreen gesture interpretation algorithms, process performance algorithms, process automation algorithms, matrix mathematics, standardization algorithms, comparison algorithms, or any other processing required to implement one or more exemplary methods and/or processes described herein. Data 18 may include, for example, variables, graphics (e.g., graphical elements, graphical areas, graphical regions, icons, buttons, windows, dialogs, pull-down menus, 3D graphics, images, animations, etc.), graphical user interfaces, alarm data, fluid data, flow rates, fluid volumes, notifications, pressures, pressure limits, blood flow, blood flow limits, fluid removal rates, fluid removal limits, target blood temperatures, blood temperature limits, heuristics indicative of malfunction, results from one or more processing programs or routines employed according to the disclosure herein, or any other data that may be necessary for carrying out the one and/or more processes or methods described herein.

In one or more embodiments, the system 10 may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The program used to implement the methods and/or processes described herein may be provided using any programmable language, or code, e.g., a high level procedural and/or object orientated programming language or code that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the system 10 may be implemented using a computer readable storage medium, configured with a computer program, where the storage medium so configured causes the computer to operate in a specific and predefined manner to perform functions described herein. Further, in at least one embodiment, the system 10 may be described as being implemented by logic (e.g., object code) encoded in one or more non-transitory media that includes code for execution and, when executed by a processor, is operable to perform operations such as the methods, processes, and/or functionality described herein.

The computing apparatus 12 may be, for example, any fixed or mobile computer system (e.g., a controller, a microcontroller, a personal computer, mini computer, etc.). The exact configuration of the computing apparatus 12 is not limiting, and essentially any device capable of providing suitable computing capabilities and control capabilities (e.g., graphics processing, control of extracorporeal blood treatment apparatus, etc.) may be used.

As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by computing apparatus 12 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by an operator.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

The methods and/or logic described in this disclosure, including those attributed to the systems, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems, devices and methods described in this disclosure may be embodied as instructions and/or logic on a computer-readable medium such as RAM, ROM, NVRAM, EEPROM, FLASH memory, magnetic data storage media, optical data storage media, or the like. The instructions and/or logic may be executed by one or more processors to support one or more aspects of the functionality described in this disclosure.

The treatment apparatus 24 may include any apparatus used by an exemplary extracorporeal blood treatment system capable of performing extracorporeal blood treatments, such as, e.g., blood circuits, sensors, pumps, reservoirs, scales, treatment sets, filters, pressure sensors, etc. For example, the treatment apparatus 24 may include one or more elements, or components, of the extracorporeal blood treatment system 100 described herein with reference to FIG. 2.

The exemplary systems, and exemplary methods performed, or used, by such exemplary systems, described herein may include systems such as, e.g., dialysis systems. The general term "dialysis" as used herein includes hemodialysis, hemofiltration, hemodiafiltration, hemoperfusion, liver dialysis, and therapeutic plasma exchange (TPE), among other similar treatment procedures. In dialysis generally, blood is taken out of the body via an arterial blood circuit and exposed to a treatment device to separate substances therefrom and/or to add substances thereto, and is then returned to the body via a venous blood circuit. Although extracorporeal blood treatment systems capable of performing general dialysis (as defined above, including TPE) shall be described herein with reference to the exemplary extracorporeal blood treatment system of FIG. 2, other systems such as those for infusion of drugs, performance of continuous renal replacement therapy (CRRT), extracorporeal membrane oxygenation (ECMO), hemoperfusion, liver dialysis, apheresis, TPE, etc. may benefit from the systems, methods, and apparatus described herein and the present disclosure is not limited to any particular treatment system.

Figure 2:
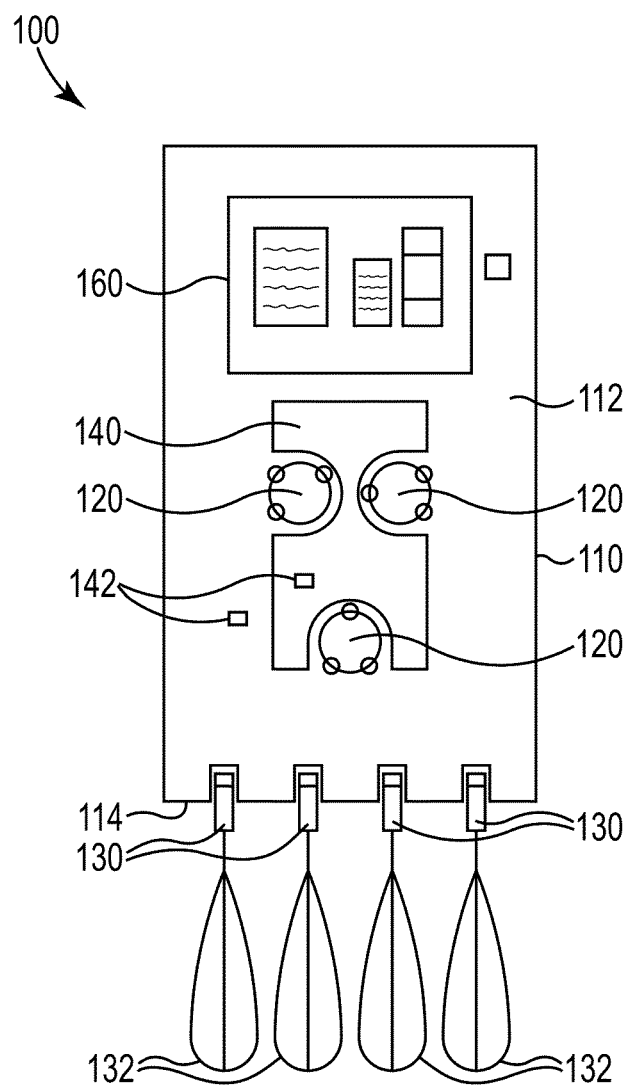
FIG. 2 is an illustration of an exemplary extracorporeal blood treatment system that may include graphical user interfaces as described herein.

Referring to FIG. 2, one illustrative embodiment of an extracorporeal blood treatment system, or apparatus, 100 is depicted. The system 100 includes a housing 110 having a front face 112. The system 100 further includes one or more pumps 120, one or more disposable elements, or integrated modules, 140, and one or more sensors 142 for use in performing one or more extracorporeal blood treatments. The one or more pumps 120 may be used to move liquids through the system as part of a treatment process. Although the pumps 120 are depicted in the form of peristaltic pumps, the pumps used in the extracorporeal blood treatment system described herein may be provided in a variety of alternative forms, e.g., piston pumps, pumps for use with syringes, diaphragm pumps, etc.

The one or more disposable elements, or integrated modules, 140 (as depicted, a single disposable element 140) may be coupled to the system 100 to, e.g., provide at least a portion of the extracorporeal blood treatment fluid circuit that may be operatively coupled to one or more other fluid circuits, one or more pumps 120, and one or more sensors 142 of the system 100 for use in performing extracorporeal blood treatments. As shown, the one or more disposable elements 140 may be coupled to the front face 112 of the housing 110 of the system 100 to, e.g., integrate with the one or more other fluid circuits, pumps 120, and sensors 142 of the system 100.

The one or more disposable elements 140 may be described as including one or more disposable fluid circuits (e.g., an extracorporeal blood treatment circuits) and one or more blood treatment units operatively coupled to the one or more disposable fluid circuits. The blood treatment units may be, for example, a plasma filter, a hemodialysis filter, a hemofiltration filter, etc. Generally, the blood treatment units may be referred to as "filter."

As described herein, the system 100 may further include one or more sensors 142. As shown, two sensors 142 are identified on the system 100. One sensor 142 is located on, or coupled to, the front surface 112 of the housing 110 and another sensor 142 is located on the, or coupled to, the disposable element 140. Additionally, the system 100 may include sensors 142 that are not visible on the outside of the housing 110, and instead, may be internal to the system 100 (e.g., within the housing 110). Generally, the system 100 may include any one or more sensors 142 so as to be able to monitor any value (e.g., any aspect, setting, level, condition, event internal to the system 100, etc.) of any process feature of the system 100 such as, e.g., process features during the performance of one or more extracorporeal blood treatments. For example, the system 100 may include one or more pressure sensors operable to measure, or monitor, various pressures of various circuits, chambers, pods, reservoirs, etc. of the system 100, e.g., during the performance of an extracorporeal blood treatment, during the performance of a pre-treatment process, during the performance of a disinfection, post-treatment process, etc. Further, for example, the system 100 may include one or more flow rate sensors operable to measure, or monitor, various fluid flow rates of fluids within various circuits, chambers, pods, reservoirs, etc. of the system 100, e.g., during the performance of an extracorporeal blood treatment, during the performance of a pre-treatment process, during the performance of a disinfection, post-treatment process, etc. Specifically, the system 100 may include one or more blood flow rate sensors to monitor various blood flow rates throughout the blood circuits of the system 100. Still further, for example, the system 100 may include other sensors 142 such as fluid level sensors, temperature sensors, leak detection sensors, etc. that may be used before an extracorporeal blood treatment is performed, during the performance of an extracorporeal blood treatment, and/or after an extracorporeal blood treatment is performed.

Additionally, the extracorporeal blood treatment fluid circuit of the system 100 may be described as being completed by a combination of the disposable element 140 and the system 100 and may be generally described as defining a blood circuit that removes blood from a patient, for example, via a catheter inserted in a vascular access of the patient, and takes the blood though a blood removal line. Then, the blood may pass through a chamber (e.g., a blood chamber) and, via a return line, may be transported back to the patient.

The extracorporeal blood treatment system 100 may also include reservoir sensors, or scales, 130 (e.g., weight sensors, load cells, etc.), each of which is configured to hold and weigh a reservoir 132. The reservoir sensors 130 are positioned below a bottom end 114 of the housing 110, at least in part because the reservoirs 132 are typically attached to and hang from the reservoir sensors 130. Although the depicted embodiment of the extracorporeal blood treatment system 100 includes four reservoir sensors, or scales, 130 and associated reservoirs 132, alternative embodiments of extracorporeal blood treatment systems as described herein may include one or more reservoir sensors 130 and associated reservoirs 132 such as, e.g., as few as two reservoirs sensors 130 and associated reservoirs 132, four or more reservoirs sensors 130 and associated reservoirs 132, etc.

The extracorporeal blood treatment system 100 also includes a display 160 used to show, or convey, information to an operator or user. The display 160 may also serve as an input device if, e.g., the display 160 is in the form of a touchscreen (e.g., a user interactable graphical user interface, etc.). Also, although the display 160 is depicted as being located in the housing 110, in one or more alternate embodiments, the display 160 may be separate from the housing 110 of the extracorporeal blood treatment system 100. For example, the display 160 may be movably (e.g., swivel, tilt, etc.) attached, or coupled, to the housing 110 (e.g., a top end of the housing 110).

As shown in FIG. 1 and as related to FIG. 2, the treatment apparatus 24 may be operatively coupled, or connected, to the computing apparatus 12. Among the treatment apparatus 24 operably coupled to the computing apparatus 12 may be the pumps 120 as shown in FIG. 2.

Exemplary graphical user interfaces, or portions thereof, for use in displaying information related to extracorporeal blood treatments, providing functionality to an operator for use in preparing and performing extracorporeal blood treatments and/or configuring or maintaining an extracorporeal blood treatment system are depicted in FIGS. 3-9. Such exemplary graphical user interfaces may be depicted by the display apparatus 22 of the system 10 described herein with reference to FIG. 1 and/or the display 160 of the system 100 of FIG. 2. Additionally, the graphical user interfaces described herein may be depicted on a touchscreen, and in such configuration, the input apparatus would also be the touchscreen.

Each exemplary graphical user interface of the exemplary extracorporeal blood treatment systems and methods described herein may include one or more graphical elements, regions, and areas used to display information to a user. An operator may use input apparatus 20 of the exemplary extracorporeal blood treatment system 10 described herein with reference to FIG. 1 to select or manipulate graphical elements, regions, and areas of the exemplary graphical user interfaces of FIGS. 3-9. As used herein, when an operator "selects" or "interacts with" a graphical element, area, and/or region of the graphical user interface, it is to be understood that "selecting" or "interacting with" the graphical element, area, and/or region to perform one or more tasks or steps may be conducted in many different ways using many different types of input apparatus. For example, when the input apparatus includes a touch screen, an operator may select or interact with a graphical element, area, and/or region by "touching" the graphical region with their finger or using a pointing device such as a stylus. Further, for example, when the input apparatus includes a mouse or similar pointing device, an operator may select or interact with a graphical element, area, and/or region by locating an arrow or cursor over the desired graphical region "clicking" the graphical region. Still further, for example, when the input apparatus includes a series of buttons and/or knobs, an operator may select or interact with a graphical element, area, and/or region by using the buttons and/or knobs to navigate to the graphical region and to select it (e.g., by depressing the button and/or knob). Additionally, it is to be understood that selection of or interaction with a graphical element, area, and/or region may be conducted using various gestures such as, for example, but not limited to, swipes, select-and-drag, press, tracing of various shapes, pinch-inwardly, pinch-outwardly, finger spread, multi-finger touches and/or swipes, etc.

Figure 3B:
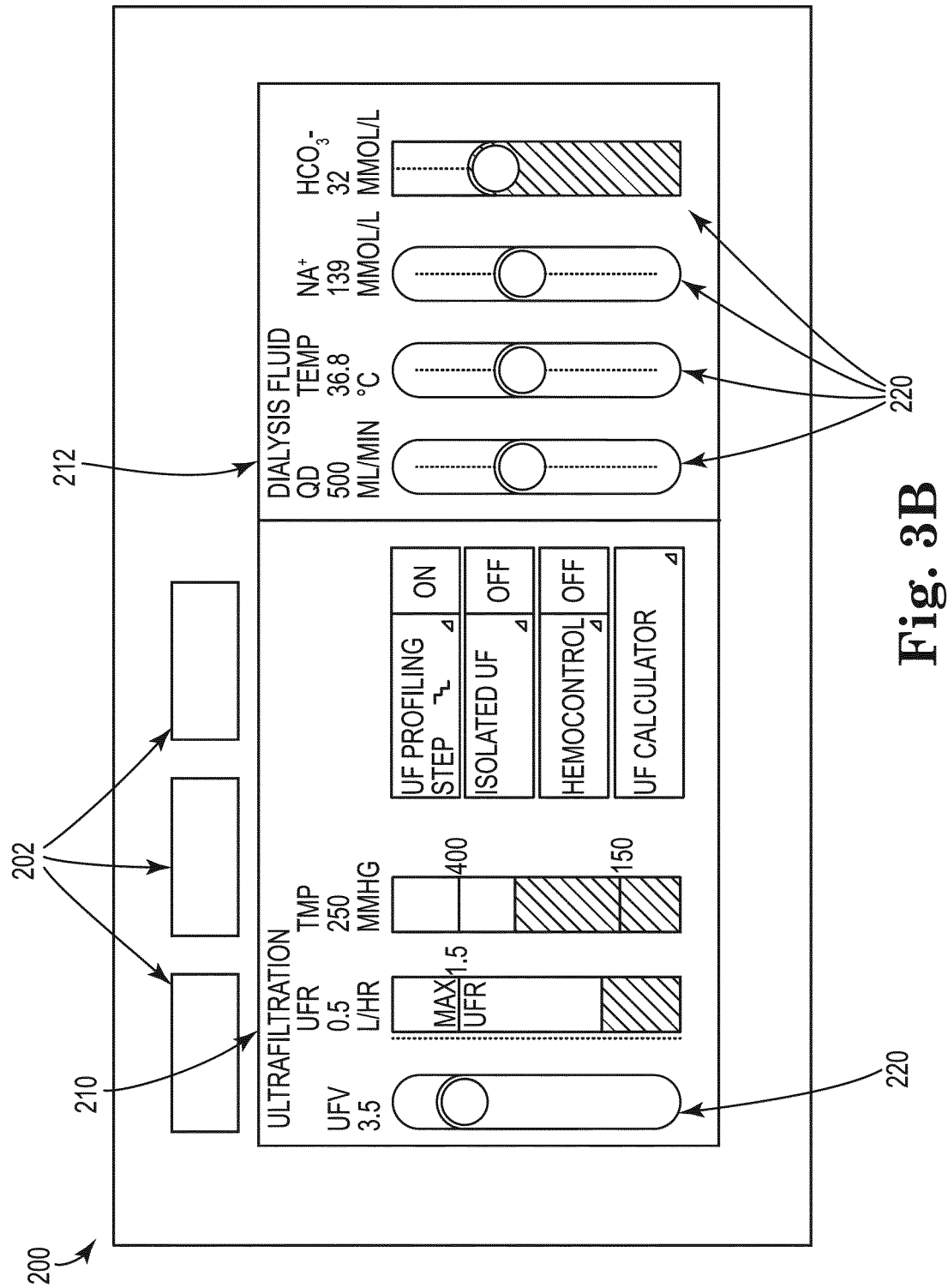

An exemplary graphical user interface 200 is depicted in FIGS. 3A-3B that may be generally used to perform one or more processes provided by an extracorporeal blood treatment system. As generally shown, the graphical user interface 200 may include a plurality of graphical regions 202 that may be used in the preparation or performance of an extracorporeal blood treatment as well as other functionality and/or processes of the extracorporeal blood treatment system. For example the graphical regions 202 may be used to indicate, initiate, revert, and stop one or more process features of processes of the extracorporeal blood treatment system. In the exemplary graphical user interface 200, each of the graphical regions 202 may correspond to (e.g., representative of, associated with, etc.) one or more processes of an extracorporeal blood treatment. For example, at least some of the graphical regions 202 related to an on-going extracorporeal blood treatment may include a blood process feature graphical region, dialysis fluid process feature graphical region, and an ultrafiltration process feature graphical region. Additionally, when a blood treatment is not being performed, such as during setup before a blood treatment is performed or during disinfection after a blood treatment is performed, the graphical regions 202 may not be directly-related to a blood treatment but instead may be related to the setup (e.g., entering of a prescription) or disinfection.

The graphical user interface 200 may be configured to display one or more parameter adjustment regions 210, 212 such as shown in FIG. 3B. The parameter adjustment regions 210, 212 may be displayed in response to a user selecting one or more of the graphical region 202 of FIG. 3A. Selection of some graphical regions 202 may display more than one parameter adjustment region such as shown in FIG. 3B while selection of some other graphical regions 202 may only display a single parameter adjustment region. In at least one embodiment, selection of a graphical region 202 may display all exemplary parameter adjustment regions that the exemplary graphical user interface 200 is configured to display.

As described herein, some of the graphical regions 202 of the graphical user interface 200 of FIG. 3A may be associated with a blood treatment being performed by the exemplary system. For example, the graphical regions 202 of the graphical user interface 200 of FIG. 3A may include a blood process feature graphical region, a dialysis fluid process feature graphical region, and an ultrafiltration process feature graphical region, and each of these graphical regions may be associated with a particular parameter adjustment region. For instance, the ultrafiltration parameter adjustment region 210 of FIG. 3B may be associated with an ultrafiltration process feature graphical region, and thus, may be displayed by selection of the ultrafiltration process feature graphical region. A user may use the ultrafiltration parameter adjustment region 210 to ascertain and/or adjust one or more parameters related to one or more ultrafiltration processes. Further, the dialysis fluid parameter adjustment region 212 of FIG. 3B may be associated with the dialysis fluid process feature graphical region, and thus, may be displayed by selection of the dialysis fluid process feature graphical region. A user may use the dialysis fluid parameter adjustment region 212 to ascertain and/or adjust one or more parameters related to one or more dialysis fluid processes (e.g., prescription-related processes). Another parameter adjustment region may include a priming adjustment region configured to allow a user to ascertain and adjust one or more parameters related to priming. Further parameter adjustment regions may include one or more parameters related to profiling settings, dialysis dose monitoring settings, hemodiafiltration settings, rinseback volume, blood pressure alarm limits, ultrafiltration settings, dialysis fluid settings, treatment time, treatment modes, blood circuit pressure settings, etc.

Each of the parameter adjustment regions such as the ultrafiltration parameter adjustment region 210 and the dialysis fluid parameter adjustment region 212 may include one or more bar-type parameter adjustment elements 220 (e.g., at least one bar-type parameter adjustment element, a plurality of bar-type parameter adjustment elements, two or more bar-type parameter adjustment elements, etc.). As shown, the ultrafiltration parameter adjustment region 210 includes a single bar-type parameter adjustment element 220 and the dialysis fluid parameter adjustment region 212 includes a plurality of bar-type parameter adjustment elements 220. The plurality of bar-type parameter adjustment elements 220 of the dialysis fluid parameter adjustment region 212 may be described as being displayed simultaneously or shown at the same time. Further, as shown, the plurality of bar-type parameter adjustment elements of the dialysis fluid parameter adjustment region 212 are aligned with each other and parallel to each other, which will be further described herein.

Each of the bar-type parameter adjustment elements 220 may be associated with and configured to adjust a parameter of a plurality of parameters of the extracorporeal blood treatment system. The plurality of parameters may be, e.g., related to an extracorporeal blood treatment (e.g., related to all or parts of a prescription for an extracorporeal blood treatment), related to extracorporeal blood treatment setup, related to disinfection of the extracorporeal blood treatment system, related to extracorporeal blood treatment system configuration, etc.

As shown in FIG. 3B, the bar-type parameter adjustment elements 220 may be associated with and configured to adjust parameters related to the parameter adjustment region located therein. For example, the bar-type parameter adjustment element 220 of, or within, the ultrafiltration parameter adjustment region 210 is associated with and configured to adjust a parameter related to ultrafiltration, namely, ultrafiltration volume. Further, for example, the bar-type parameter adjustment elements 220 of, or within, the dialysis fluid parameter adjustment region 212 are associated with and configured to adjust parameters (e.g., parameters of a prescription) related to dialysis fluid, namely, dialysis fluid flow (QD) rate, temperature, Sodium (Na+) concentration, and bicarbonate ($HCO_3^-$) concentration. Still further, for example, bar-type parameter adjustment elements 220 may be associated with and configured to adjust parameters related to profile settings, temperature settings, dialysate settings, dialysis dose monitoring settings, and/or rinse-back settings.

A bar-type parameter adjustment element 220 of the dialysis fluid parameter adjustment region 212 will be described in more detail with respect to FIGS. 4-9 and will be further referred to as the dialysis fluid flow rate bar-type parameter adjustment element 220. It is to be understood that the functionality and elements described with respect to the dialysis fluid flow rate bar-type parameter adjustment element 220 may apply to any of the exemplary bar-type parameter adjustment elements 220.

As shown in FIG. 4, the dialysis fluid flow rate bar-type parameter adjustment element 220 may include a bar element 221 extending from a first, or lower, end 222 to a second, or upper, end 224, and an indicator element 225 located along the bar element 221 between the first end 222 and the second end 224. The bar element 221 may define a length 230 from the first end 222 to the second end 224, which may define, or correspond to, a range of dialysis fluid flow rate values.

As described previously, a plurality of bar-type parameter adjustment elements 220 may be described as being aligned with each other, which, more specifically, may mean that the first ends 222 of the aligned bar-type parameter adjustment elements 220 may lie in a line and the second ends 224 of the aligned bar-type parameter adjustment elements 220 may also lie in a line to provide an "equalizer"-style of parameter display and adjustment. In other words, the plurality of bar-type parameter adjustment elements 220 may extend the same distance in the same direction and may be arranged next to each other in a parallel fashion.

The indicator element 225, or more specifically, the location of the indicator element 225 along the bar element 221, may indicate a present value of the associated parameter, which, in this example, is the dialysis fluid flow rate. Although as shown, the indicator element 225 is a circular, button-type graphical element, the indicator element 225 may be any graphical element recognizable by a user as indicating the present value of the associated parameter and usable to adjust the associated parameter. Additionally, as will be described further herein, the indicator element 225 may be graphically emphasized to draw a user's attention during adjustment. More specifically, the indicator element 225 may change size, color, and/or shape and/or be animated after being selected for adjustment, and may revert back to its original state after adjustment is complete.

The dialysis fluid flow rate bar-type parameter adjustment element 220 further includes an alphanumeric depiction 229 of the associated value. As shown, the alphanumeric depiction 229 of the associated value, which is dialysis fluid flow rate (QD), indicates that the present value is 500 milliliters per minute (ml/min).

The exemplary systems and methods described herein may further include a reference value for each of the parameters associated with the bar-type parameter adjustment elements 220. Each reference value may represent a selected prescription value, a preset default value, or a saved value for a patient. For example, a prescription may be entered in an exemplary extracorporeal treatment system prior to treatment and/or during setup of a treatment, and the prescription may include a reference value for one or more parameters of the treatment. Further, for example, if a reference value is not provided for a parameter via a prescription or another process, the reference value may be set based on a default value for the parameter saved in the exemplary system. Still further, for example, the exemplary system may include saved data such as, e.g., previous treatment or prescription data, etc. for a patient, and the reference values for one or more parameters may be based upon the saved data.

A user may be able to view the bar-type parameter adjustment elements 220 to quickly determine whether the present associated values are different than the reference values associated therewith. To provide this functionality, the bar-type parameter adjustment elements 220 may be scaled such that a midpoint 231 between the first, or lower, end 222 and the second, or upper, end 224 of the bar element 221 may be representative of the reference value for the associated parameter. The midpoint 231 may be defined as the area located approximately half-way between the first end 222 and the second end 224. Further, it may be described that the range shown by the bar-type parameter adjustment elements 220 may be adjusted to account for the reference value associated therewith such that the midpoint 231 of the bar element 221 is representative of the reference value. As such, due to the scaled nature of the bar-type parameter adjustment elements 220, a user may quickly ascertain upon viewing each bar-type parameter adjustment element 220 whether the present value of a parameter associated with the bar-type parameter adjustment element 220 is greater than, less than, or equal to the reference value by determining whether the indicator element 225 is "above" the midpoint 231, "below" the midpoint 231, or "at" the midpoint 231, respectively. In other words, the range of values depicted by the bar-type parameter adjustment elements 220 may be adjusted, or configured, to locate the reference value of the associated parameter at the midpoint 231 of the bar element 221.

Figure 4A:
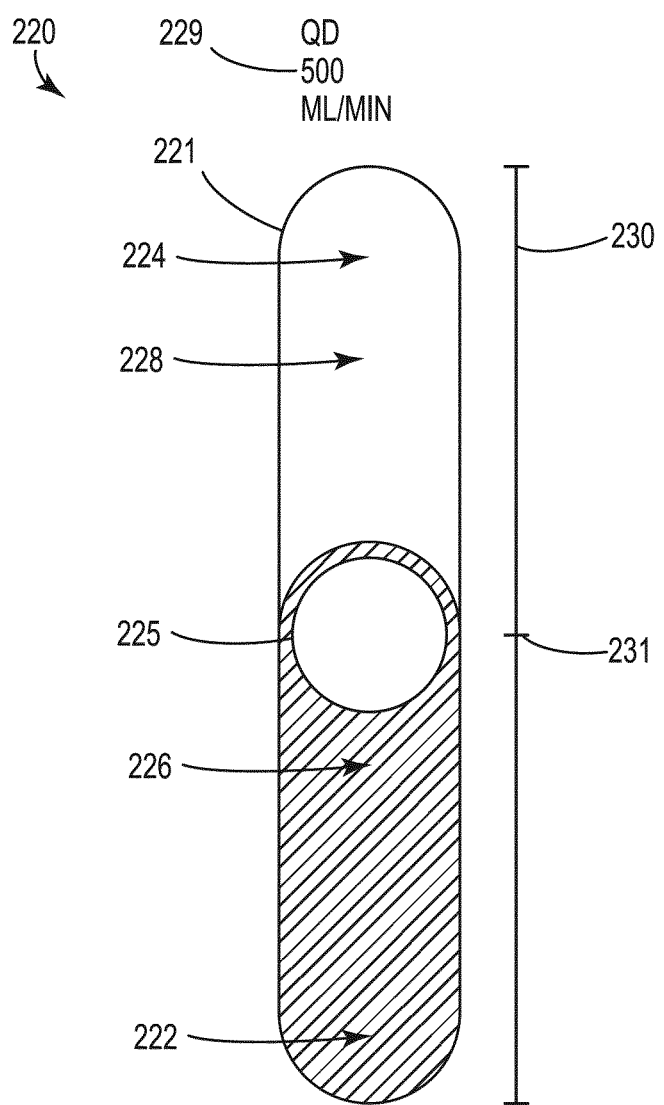
FIGS. 4A-4D depict an exemplary bar-type parameter adjustment element of FIG. 3B.

For example, as shown in FIG. 4A, the indicator element 225 is located at the midpoint 231 of the bar element 221 thereby indicating to a user that the dialysis fluid flow rate value is presently at the reference value, which is 500 ml/min. If the indicator element 225 were located closer to the first end 222 than the second end 224, such location of the indicator element 225 would indicate to a user that the parameter is less than the reference value. If the indicator element 225 were located closer to the second end 224 than the first end 222, such location of the indicator element 225 would indicate to a user that the parameter is greater than the reference value.

In one or more embodiments, the scale and/or length 230 of the bar elements 221 of the bar-type parameter adjustment elements 220 may not allow the midpoints 231 to be representative of the reference value, and the size and/or positioning of the bar elements 221 may be adjusted or configured to compensate therefore. For example, the lengths 230 of the bar element 221 may be adjusted (e.g., increased or decreased) such that the midpoint 231 of the bar element 221 is associated with the reference value. Further, for example, the position of the bar elements 221 with respect to other bar elements 221 may be shifted with respect to each other such that the references values associated therewith align perpendicularly to the bar elements 221. In other words, the first and second end 222, 224 of the bar elements 221 of the plurality of bar-type parameter adjustment elements 220 may not align when the plurality of bar-type parameter adjustment elements 220 are shifted such that reference values associated therewith are aligned perpendicularly to the bar elements 221.

A user may adjust a parameter associated with a bar-type parameter adjustment element 220 using one or more various processes, each of which may adjust the parameter differently. For example, some adjustment processes may be used for "fine" adjustment of a parameter, and some adjustment processes may be used for "coarse" adjustment of a parameter.

Figure 4B:
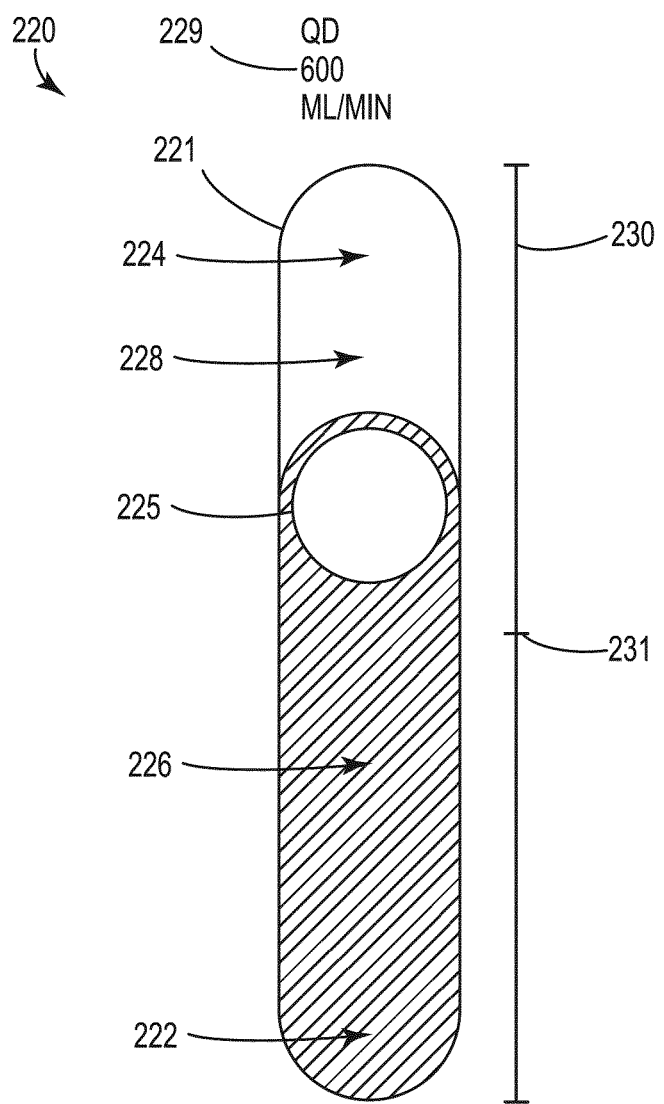

In one or more embodiments, a user may adjust a parameter associated with a bar-type parameter adjustment element 220 by selecting (e.g., touching, clicking, etc.) and dragging (e.g., moving without un-selecting) the indicator element 225 towards the first end 222 along the bar element 221 to decrease the parameter and selecting and dragging the indicator element 225 towards the second end 224 along the bar element 221 to increase the parameter. For example, as shown in FIG. 4B, a user has selected and dragged the indicator element 225 towards the second end 224 of the bar element to increase the dialysis fluid flow rate to 600 ml/min. As shown, the indicator element 225 is now closer to the second end 224 than the first end 222, which indicates that the present value of dialysis fluid flow rate, i.e., 600 ml/min, is greater than the reference value, i.e., 500 ml/min. Further, a user may quickly ascertain that the dialysis fluid flow rate is greater than the reference value because the indicator element 225 is located "above" the midline 231.

Figure 4C:
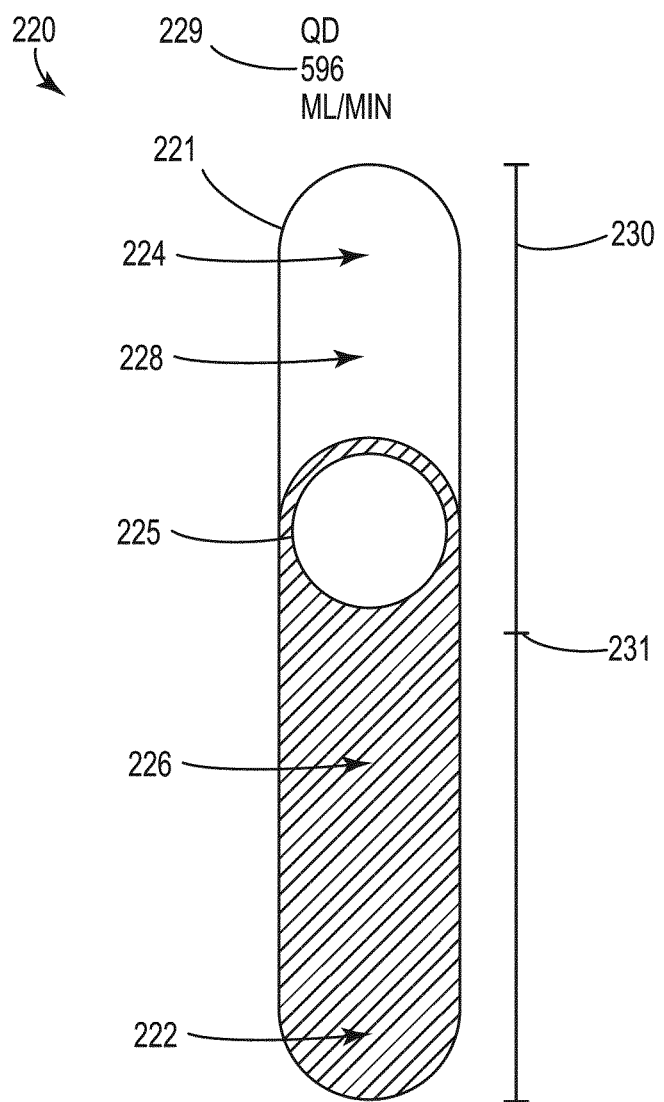

In one or more embodiments, a user may adjust a parameter associated with a bar-type parameter adjustment element 220 by selecting (e.g., touching) and releasing a first area 226 (e.g., a select-and-release may be a "tap" or a momentary "touch") defined between the indicator element 225 and the first end 222 of the bar element 221 to decrease the parameter by a finite value and selecting and releasing a second area 228 defined between the indicator element 225 and the second end 224 of the bar element 221 to increase the parameter by the finite value. For example, as shown in FIG. 4C, a user has selected the first area 226 between the indicator element 225 and the first end 222 to decrease the dialysis fluid flow rate by 4 ml/min to 596 ml/min. In other words, the selection of the first area 226 decreased the present dialysis fluid flow rate by the finite value of 4 ml/min.

The finite value, or amount, upon which the present value may be increased or decreased by selection of the first area 226 or second area 228 may vary depending on the parameters being adjusted. Thus, the finite amount, or value, may be expressed as a step percentage of the total range depicted by the bar element 221. For example, the bar element 221 of the dialysis fluid bar-type parameter adjustment element 220 may extend from 0 ml/min to 1000 ml/min, and the finite adjustment value, or amount, may be 4 ml/min as shown in FIG. 4C, which may be expressed as 0.4% of the total range, i.e., 1000 ml/min, depicted by the bar element 221. In one or more embodiments, the step percentage (e.g., upon which the present value may be increased or decreased by selection of the first area 226 or second area 228) may be greater than or equal to 0.1% of the total range depicted by the bar element 221, greater than or equal to 0.2% of the total range depicted by the bar element 221, greater than or equal to 0.3% of the total range depicted by the bar element 221, greater than or equal to 0.5% of the total range depicted by the bar element 221, greater than or equal to 0.9% of the total range depicted by the bar element 221, greater than or equal to 1% of the total range depicted by the bar element 221, greater than or equal to 3% of the total range depicted by the bar element 221, greater than or equal to 5% of the total range depicted by the bar element 221, etc. In one or more embodiments, the step percentage (e.g., upon which the present value may be increased or decreased by selection of the first area 226 or second area 228) may be less than or equal to 15% of the total range depicted by the bar element 221, less than or equal to 12.5% of the total range depicted by the bar element 221, less than or equal to 10% of the total range depicted by the bar element 221, less than or equal to 8% of the total range depicted by the bar element 221, less than or equal to 6% of the total range depicted by the bar element 221, less than or equal to 4.5% of the total range depicted by the bar element 221, less than or equal to 3.5% of the total range depicted by the bar element 221, less than or equal to 2.5% of the total range depicted by the bar element 221, less than or equal to 1.5% of the total range depicted by the bar element 221, less than or equal to 0.8% of the total range depicted by the bar element 221, etc.

Further, the finite value, or amount, upon which the present value may be increased or decreased by selection of the first area 226 or second area 228 may also be preset incremental value (e.g., selected or customized for each different parameter). The preset incremental value may not be so large to negatively affect an on-going blood treatment due to accidental increment or decrement by the present incremental value.

The "select and drag"-style of parameter adjustment may be referred to as a "coarse" adjustment process because, e.g., the parameter may be adjusted by greater increments across a broader range than the "select an area"-style of parameter adjustment. The "select an area"-style of parameter adjustment may be referred to as a "fine" adjustment process because, e.g., the parameter may be adjusted by smaller increments (e.g., finite values) than the "select and drag"-style of parameter adjustment.

Figure 4D:
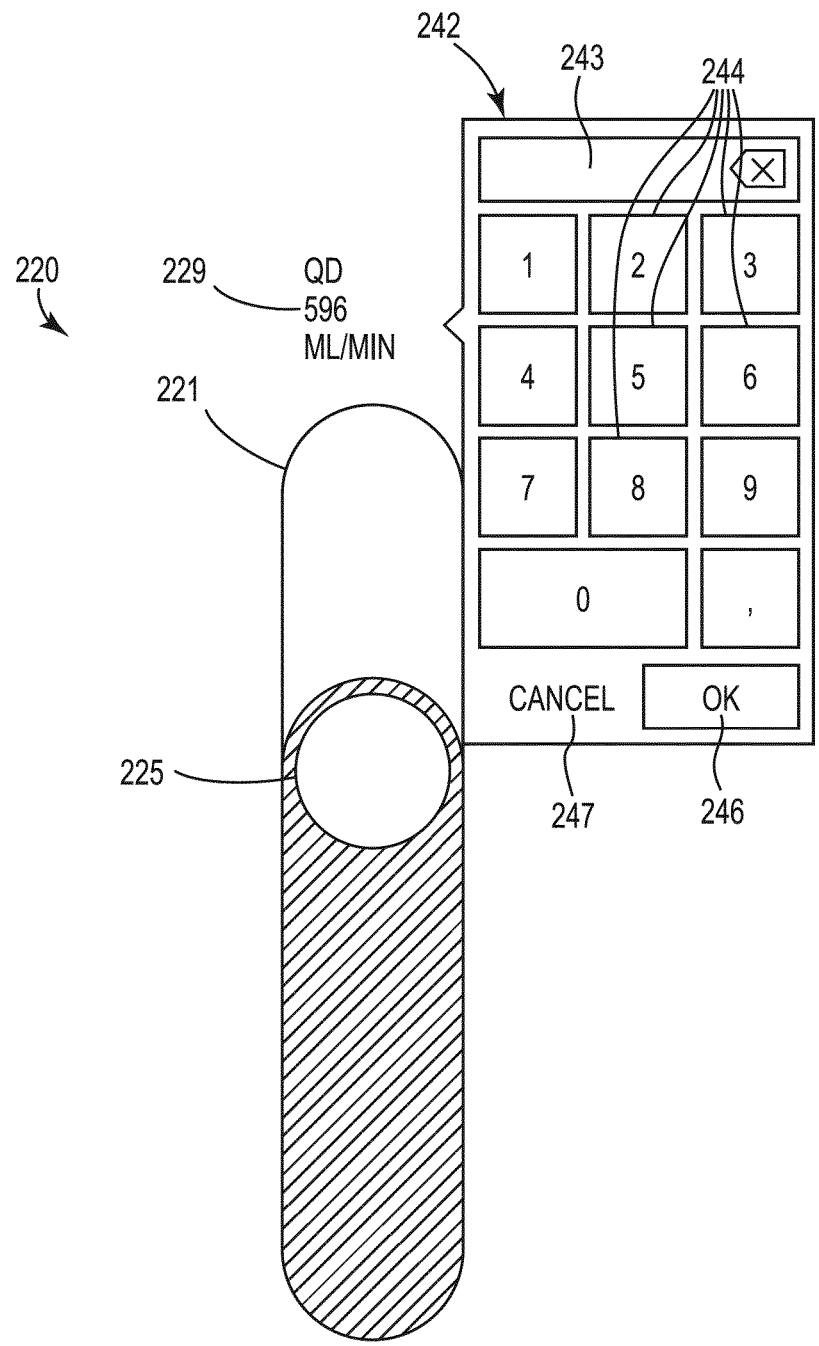

The exemplary bar-type parameter adjustment elements 220 may further include another method or process for parameter adjustment using the alphanumeric depiction 229. For example, upon selection of the alphanumeric depiction 229, an alphanumeric parameter entry region 242 may be displayed as shown in FIG. 4D. In other words, the alphanumeric parameter entry region 242 may be displayed in response to the selection (e.g., touch, click, tap, etc.) of the alphanumeric depiction 229. The alphanumeric parameter entry region 242 may include a plurality of selection areas (e.g., buttons, squares, etc.) 244 configured to allow a user to enter a parameter value and a confirmation area 246 configured to allow a parameter value to be entered. More specifically, the plurality of selections areas 244 may each represent and be associated with a number from 0-9 such that selection thereof may enter the number associated therewith. The present entered value, e.g., entered using the selection areas 244, may be further depicted in an entered value area 243 of the alphanumeric parameter entry region 242. Thus, a user desiring to change the associated parameter of the bar-type parameter adjustment element 220 may select the alphanumeric depiction 229 to display the alphanumeric parameter entry region 242. Then, the user may use the selection areas 244 to enter a value that is displayed in the entered value area 243 and the user may confirm the value by selecting the confirmation area 246. If a user decides not to enter a value using the alphanumeric parameter entry region 242, the user may select the cancellation area 247, which may remove the alphanumeric parameter entry region 242 from the graphical user interface.

Users may mistakenly adjust one or more parameters using graphical user interfaces by, e.g., selecting the incorrect parameter, adjusting a parameter to an incorrect value, accidentally adjusting a parameter through inadvertent selections, etc. For example, in the case of a touchscreen, a user may accidentally "drag and select" an indicator element 225 of bar-type parameter adjustment element 220 or "select an area" along a bar element 221 of a bar-type parameter adjustment element 220 by accidentally touching a portion of a touchscreen thereby inadvertently changing the value of the parameter associated therewith.

To reduce any mistakes, the exemplary systems and methods may further include various processes and functionality that assist a user in making an intended change of a parameter. For example, the exemplary systems and methods described herein may use a confirmation time period and/or a ghost element 270 to assist a user in making an intended change to a parameter using the exemplary bar-type parameter adjustment elements 220 as shown in FIGS. 5-7. Each of FIGS. 5-7 depicts the same dialysis fluid bar-type parameter adjustment element 220 over a sequential time period as will be described further herein.

Figures 5A, 5B, 5C, 5D, 5E, 5F:
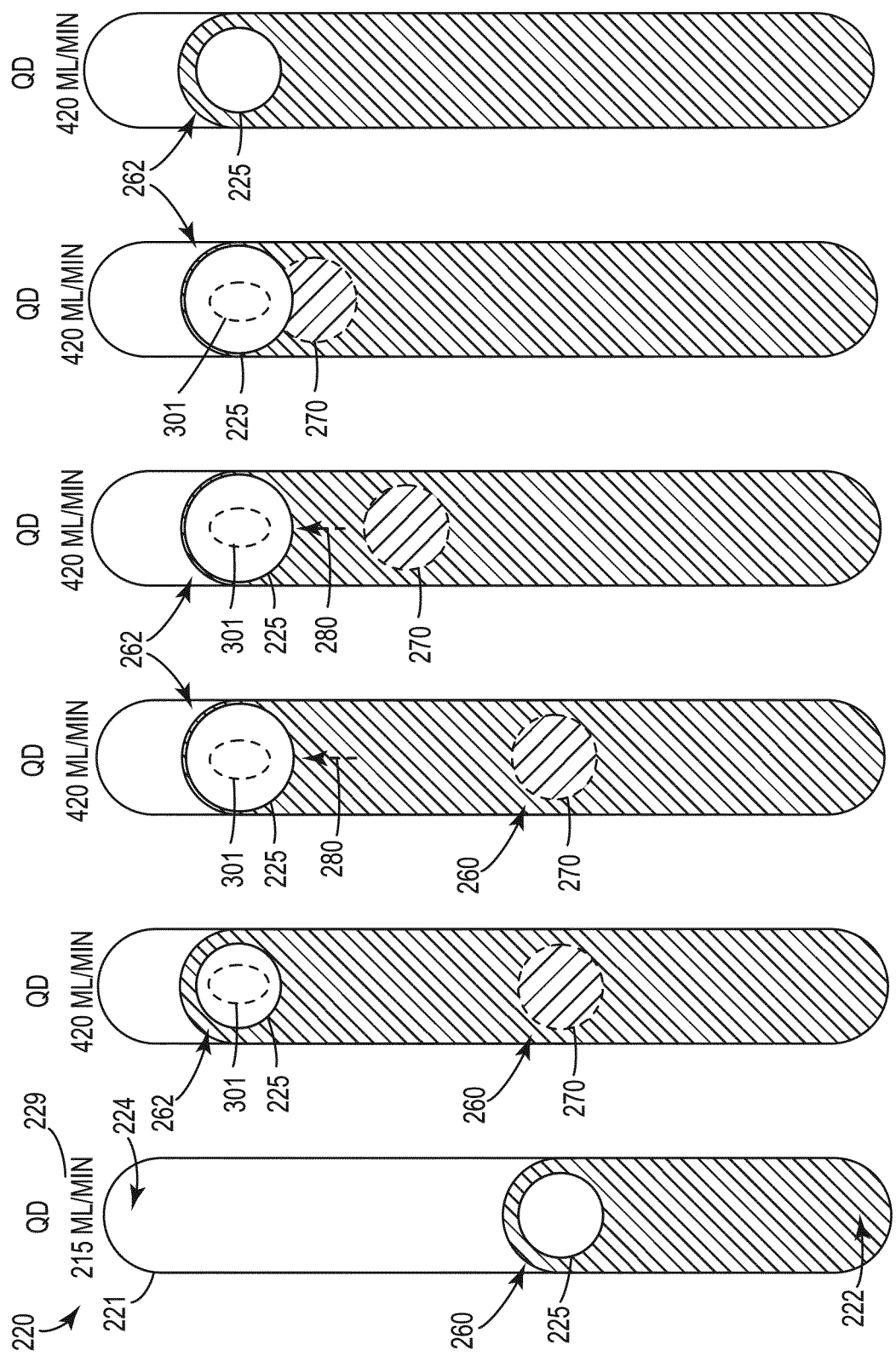
FIGS. 5-9 depict exemplary functionality of the bar-type parameter adjustment element of FIGS. 3B and 4A-4D.

The dialysis fluid bar-type parameter adjustment element 220 as shown in FIG. 5A includes an indicator element 225 located closer to the first end 222 than the second end 224 indicating a dialysis fluid flow rate less than the reference value. For a reference point, the indicator element 225 may be described as being located along the bar element 221 at a first location 260. As enumerated by the alphanumeric depiction 229, the present value of dialysis fluid flow rate is 215 ml/min.

A user has selected the indicator element 225 in FIG. 5B as shown by a dotted-line, oval 301 and dragged the indicator element 225 towards to the second end 224 to a second location 262 to initiate an increase to the dialysis flow rate to 420 ml/min. The selection and movement of the indicator element 225 in FIG. 5B to the second location 262 has not changed the dialysis fluid flow rate yet, but instead, has only initiated, or began, the adjustment process. As the user moves the indicator element 225, the alphanumeric depiction 229 may change such that user may visualize, or see, the numerical value of the proposed adjustment the parameter.

To complete, or finalize, the parameter adjustment to the dialysis fluid flow rate, a user may maintain the selection (e.g., when using a touchscreen, users may maintain contact of their finger to the indicator element 225) of the indicator element 225 at the second location 262 for a confirmation time period. After the confirmation time period elapses or expires, the parameter is changed and the user may unselect, or release their selection, of the indicator element 225. In one or more embodiments, the confirmation time period may be greater than or equal to about 100 milliseconds (ms), greater than or equal to about 150 ms, greater than or equal to about 250 ms, greater than or equal to about 350 ms, greater than or equal to about 450 ms, greater than or equal to about 550 ms, greater than or equal to about 750 ms, greater than or equal to about 1 second, greater than or equal to about 1.5 seconds, greater than or equal to about 2.0 seconds, greater than or equal to about 2.5 seconds, etc. In one or more embodiments, the confirmation time period may be less than or equal to about 200 ms, less than or equal to about 300 ms, less than or equal to about 400 ms, less than or equal to about 500 ms, less than or equal to about 600 ms, less than or equal to about 900 ms, less than or equal to about 1.25 second, less than or equal to about 1.75 seconds, less than or equal to about 2.25 seconds, etc.

Further, after a user has selected and dragged the indicator element 225 as shown in FIG. 5B, a ghost element 270 may be displayed, or depicted, at the first location 260 where the indicator element 225 was previously located along the bar element 221 (such that, e.g., an user may see where the indicator element 225 was located in reference to the new position of the indicator element 225). The ghost element 270 may be any graphical element that may indicate to a user where the indicator element 225 had been previously-located. In one or more embodiments, the ghost element 270 may be a semi-transparent representation of the indicator element 225. In other embodiments, the ghost element 270 may have a different shape or size than the indicator element 225. For example, the ghost element 270 may be a square while the indicator element is a circle. Further, in other embodiments, the ghost element 270 may have a different color or may be animated differently than the indicator element 225. For example, the ghost element 270 may be flashing or blinking while the indicator element 225 is constant.

Additionally, after a user has selected and dragged the indicator element 225 to the second location 262, the indicator element 225 may be graphically emphasized as shown in FIG. 5C. In this embodiment, the size of the indicator element 225 has been increased to, e.g., show that the indicator element 225 is presently in an adjustment state.

The ghost element 270 may not appear, or be displayed, and/or the indicator element 225 may not be emphasized immediately after, or in immediate response to, the indicator element 225 being moved as shown in FIG. 5B. Instead, the ghost element 270 may not appear and/or the indicator element 225 may not be emphasized until the user has maintained the indicator element 225 at the second location 262 for a delay, or lag, time period, which is shorter than the confirmation time period. In one or more embodiments, the delay time period may be greater than or equal to about 50 ms, greater than or equal to about 75 ms, greater than or equal to about 100 ms, greater than or equal to about 125 ms, greater than or equal to about 150 ms, greater than or equal to about 250 ms, greater than or equal to about 150 ms, etc. In one or more embodiments, the delay time period may be less than or equal to about 500 ms, less than or equal to about 300 ms, less than or equal to about 200 ms, less than or equal to about 112 ms, less than or equal to about 88 ms, less than or equal to about 63 ms, etc.

After the user has maintained selection of the indicator element 225 at the second location 262 (e.g., for the delay time period), the ghost element 270 may be displayed and may begin moving 280 as shown in FIGS. 5C-5E towards the indicator element 225 (and second location 262) to indicate to a user the length of the confirmation time period, which, in turn, may indicate to a user when the expiration of the confirmation time periods occurs. For example, when the ghost element 270 reaches the indicator element 225 (e.g., when the ghost element 270 touches, or contacts, the indicator element 225, when the ghost element 270 partially overlaps or fully overlaps the indicator element 225, etc.), a user may release (e.g., un-selected, stop maintaining contact, etc.) the indicator element 225, which will complete, or finalize, the adjustment of the parameter (e.g., confirm that the user wanted to make the adjustment). As shown in FIG. 5F, a user has released the indicator element 225 from selection, e.g., as shown by the lack of the user selection representation 301. In response to the selection and maintenance of the selection for the first, or configuration, time period at the second location 262, the indicator element 225 has reverted the graphical emphasis, e.g., decreased in size to the normal state, and the dialysis fluid flow rate has been changed to 420 ml/min as indicated by the alphanumeric depiction 229.

Generally, when after the first selected period of time elapses or expires, a notification may be provided to the user to notify the user that the first selected time period has expired. The notification may include a visual, auditory, and/or haptic notification. For example, one or more graphical animations or graphical elements may be displayed on the graphical user interface 200 to indicate that the first selected period of time has elapsed. Further, for example, the indicator element 225 may be graphically modified or animated to indicate that the first selected period of time has elapsed. As described herein, the indicator element 225 may be graphically emphasized while being maintained at the second location 262, and thus, the notification may include a de-emphasization of the indicator element 225 to a default, or un-emphasized, state. For example, the indicator element 225 may change color during user selection and may again change color (e.g., such as reversion back to its original color) upon, or in response to, expiration of the first selected period of time. In other embodiments, the graphical form such as, e.g., size, shape, etc. of the indicator element 225 may change in response to selection and/or expiration the first selected period of time. As shown in FIGS. 5-7, the graphical size of the indicator element 225 increases to provide graphical emphasis while a user is maintaining selection of the indicator element 225 at the second location 262 and decreases in response to the expiration of the confirmation time period. Further, auditory notifications of expiration of the first selected period of time may include sounds, verbal commands, etc. and haptic notifications of expiration of the first selected period of time may include vibrations, etc.

In other words, to adjust an initial value of a parameter, a user may touch a touchscreen, and without interrupting contact with the touchscreen, slide the indicator element, or "slider handle," 225 to a new value. A ghost element, or "ghost image" of the "slider handle," 270 may be shown at the location of the initial value, which is part of the exemplary undo functionality described further herein. When the user has held the indicator element 225 stationary, or still, for at least the confirmation time period, or specified confirmation timeout, the indicator element 225 may indicate to the user that the value is considered to be confirmed by altering its appearance (e.g., change form, change in color, etc.). The ghost element 270 may become animated and start moving towards the indicator element 225 at the confirmed value. The ghost element 270 may move on its way towards the indicator element 225 at the confirmed value, illustrating that undo is no longer possible until the ghost element 270 disappears under the indicator element 225 at the confirmed value. Lastly, in response to the user releasing the touchscreen, the value may be accepted for further processing, and the indicator element may return to its default appearance.

Figures 6A, 6B, 6C:
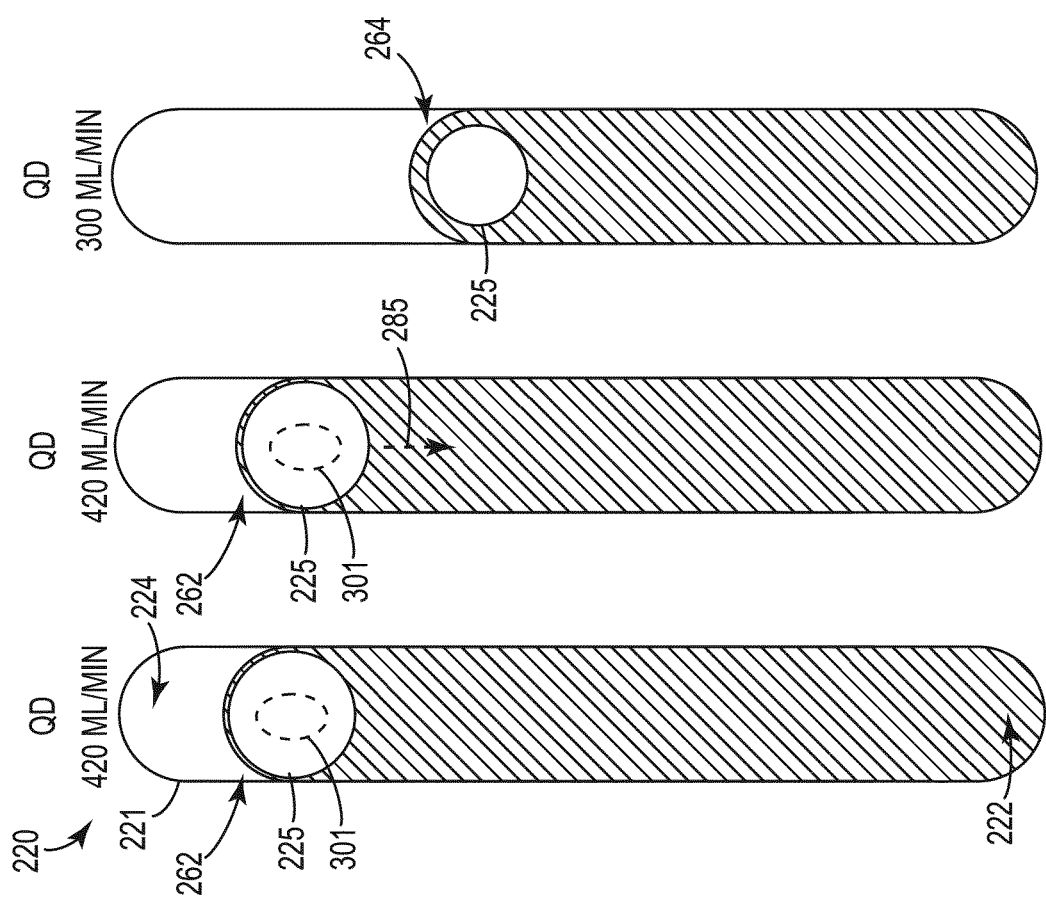

If a user would like to make a change to the parameter while maintaining selection of indicator element 225 and after the ghost element 270 has reached the indicator element 225, a user may drag, or move, the indicator element 225 while still maintaining selection of the indicator element 225 to a third location 264 (and thus, a new parameter value) as shown in FIGS. 6A-6C without initiating, or starting, another confirmation time period and/or re-displaying the ghost element 270. More specifically, the depiction in FIG. 6A may follow FIG. 5E except instead of releasing the indicator element 225 as occurs in FIG. 5F, the user may maintain selection of the indicator element 225 and drag, or move, the indicator element 225 in a direction 285 as labeled in FIG. 6B towards the first end 222 to a third location 264 as shown in FIG. 6C. After the user has adjusted the parameter to the desired value by moving the indicator element 225 to the third location 264, the user may release the indicator element 225 as shown in FIG. 6C (e.g., shown by the lack of the user selection representation 301), which may complete, or finalize, the adjustment of the parameter. After the user releases the indicator element 225, the indicator element 225 may be de-emphasized by decreasing the size of the indicator element 225 to its normal state. In this example in FIG. 6C, the dialysis fluid flow rate has been set, or adjusted to, 300 ml/min.

In other words, FIGS. 6A-6C show the adjustment of a parameter value after the confirmation time period has been reached. Generally, instead of directly releasing the indicator element, or "slider handle," 225 when it indicates the value is confirmed (e.g., through a notification, through the ghost element 270 reaching the indicator element, etc.), the user may decide to make further adjustments. To do so, the user may maintain, or keep, in constant contact with the touch-screen (e.g., selecting the indicator element 225) and may then freely move the indicator element 225 to any position on the bar element, or slider, 221. When the user eventually releases contact with the touchscreen, the value may be accepted immediately for further processing as the user has already confirmed the indicator element 225 by holding it stationary, or still, for the confirmation time period.

Figures 7A, 7B, 7C, 7D, 7E:
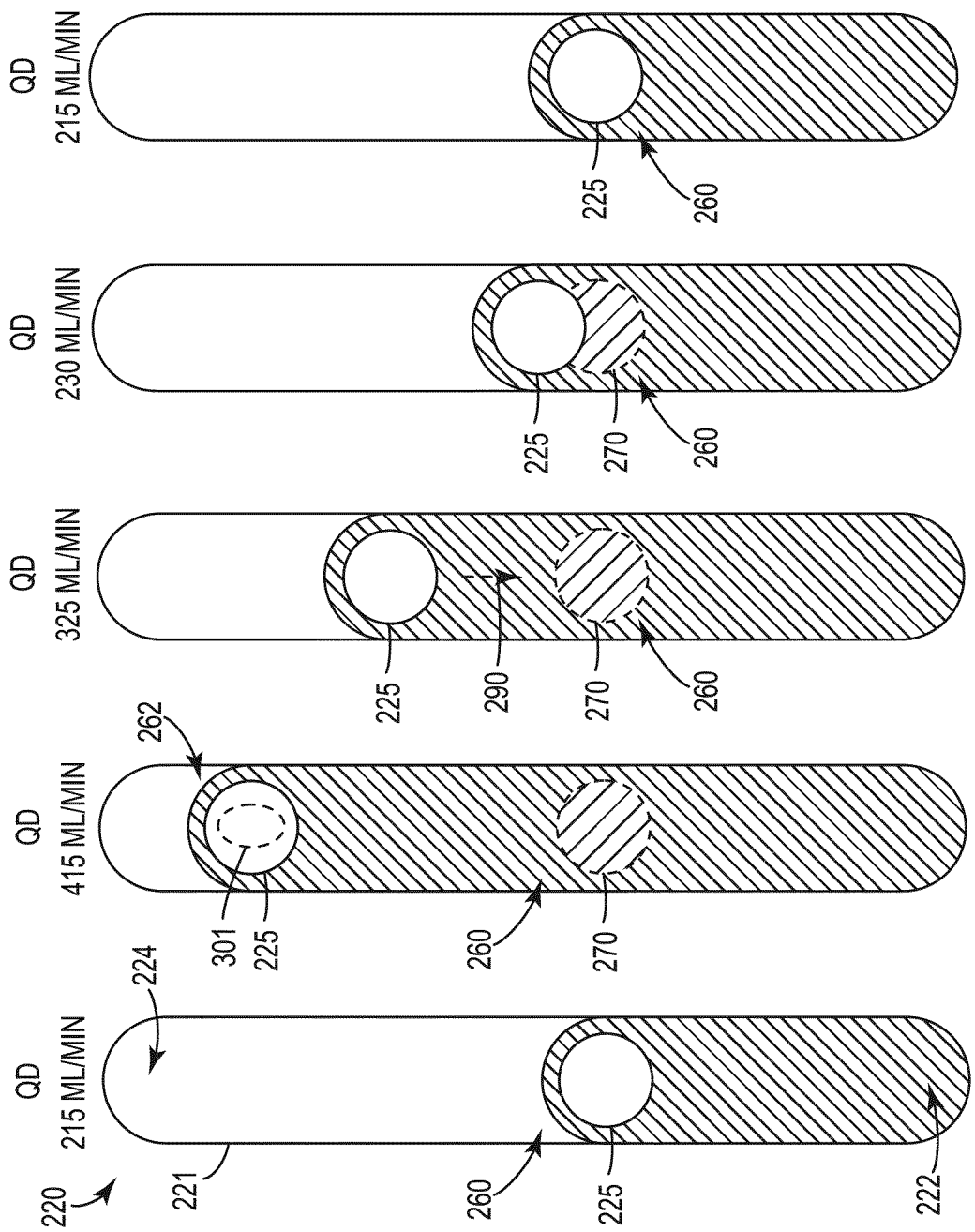

When a user releases selection of the indicator element 225 prior to the confirmation time period expiring, or elapsing, and prior to the ghost element 270 reaching the indicator element 225 (and second location 262), the indicator element 225 may return to the first location 260 and the parameter will not be changed as shown in FIGS. 7A-7E. As show in FIG. 7A, the indicator element 225 is located at the first location 260 indicating a dialysis fluid flow rate of 215 ml/min. A user has selected and dragged the indicator element 225 to the second location 262 and a ghost element 270 has been displayed in FIG. 7B. Before the ghost element 270 has begun moving and before the indicator element 225 has become graphically emphasized (e.g., increase in size), a user has released the indicator element 225 (e.g., un-selected the indicator element 225, released contact with the indicator element 225, etc.). In response to releasing the indicator element 225, the indicator element 225 has begun moving in direction 290 back towards the first location 260 as shown in FIGS. 7C-7D. The indicator element 225 has completely moved back to the first location 260 in FIG. 7E and the parameter has not been adjusted in response to the selection and movement of the indicator element 225 shown in FIG. 7B.

In other words, the adjustment of the value was abandoned and a subsequent undo was performed in FIGS. 7A-7E. In this scenario, the user starts moving the indicator element, or "slider handle," 225 to adjust the associated parameter value but decides to abandon the change. First, the user starts moving the indicator element 225 and a ghost element, or "ghost representation" of the "slider handle," 270 is created at the original starting point to illustrate the original value (e.g., in response to the user moving the indicator element 225). When the user releases the indicator element 225, it will return to the original starting point since the value was not confirmed by holding the indicator element 225 still, or stationary, for the confirmation time period.

The undo functionality described herein with respect to FIGS. 7A-7E may be described as both assistance to the user and a safety feature. The parameter value cannot be changed unless the confirmation time period has been reached by holding the "slider handle" stationary, which may prevent accidental large value updates because of a single accidental touch.

To reduce accidental adjustments of parameters associated with the bar-type parameter adjustment elements 220, the exemplary systems and methods may further include various processes and functionality that ensure that a user intended to make any such changes. For example, the exemplary systems and methods described herein may use an indicator element that is configurable in locked state and unlocked state as shown in FIGS. 8A-8E. Each of FIGS. 8A-8E depicts the same dialysis fluid bar-type parameter adjustment element 220 over a sequential time period as will be described further herein.

The indicator element 225 in the bar-type parameter adjustment element 220 of FIGS. 8A-8E may be configurable in a locked state and in an unlocked state. When the indicator element 225 is configured in the locked state, the indicator element 225 may not be movable (e.g., selectable-and-draggable) by a user to adjust the associated parameter of the bar-type parameter adjustment element 220. For example, if a user inadvertently selects (e.g., touches, taps, momentarily selects, etc.) the indicator element 225 when the indicator element 225 is in the locked state, the indicator element 225 may not move or be able to be moved. To ensure that a user has not inadvertently, or accidentally, selected the indicator element 225, the indicator element 224 may remain in the locked state until a user configures the indicator element 224 into the unlocked state. In other words, the locked state may be a default state, or configuration, for the indicator element 220, which may be changed by deliberate user action. In at least another embodiment, the exemplary system may configure the indicator element 225 into the unlocked state in response to one or more events (e.g., alarms, etc.) without user action to, e.g., expedite any changes to be made to the associated parameters. In other words, one or more events such as an alarm may occur, which may trigger the unlocking of the indicator element 224 such that a user may select and move the indicator element 224 without first unlocking it.

When the indicator element 225 is configured in the unlocked state, the indicator element 225 may be movable (e.g., selectable-and-draggable) by a user to adjust the associated parameter of the bar-type parameter adjustment element 220. To place, or configure, the indicator element 225 into the unlocked state, a user may perform a deliberate action. For example, in the embodiment depicted in FIGS. 8A-8E, a user may be select the indicator element 225 and maintain selection of the indicator element 225 for an unlock time period. If the user has maintained selection of the indicator element 225 until expiration of the unlock time period, the indicator element 225 may be configured into the unlocked state and the user may be free to move (e.g., drag) the indicator element 225 along the bar element 221 towards the first end 222 or the second end 224 along the bar element to decrease or increase, respectively, the associated parameter.

In one or more embodiments, the unlock time period may be greater than or equal to about 100 ms, greater than or equal to about 150 ms, greater than or equal to about 250 ms, greater than or equal to about 350 ms, greater than or equal to about 450 ms, greater than or equal to about 550 ms, greater than or equal to about 750 ms, greater than or equal to about 1 second, greater than or equal to about 1.5 seconds, greater than or equal to about 2.0 seconds, greater than or equal to about 2.5 seconds, etc. In one or more embodiments, the unlock time period may be less than or equal to about 200 ms, less than or equal to about 300 ms, less than or equal to about 400 ms, less than or equal to about 500 ms, less than or equal to about 600 ms, less than or equal to about 900 ms, less than or equal to about 1.25 second, etc. In at least one embodiment, the unlocked time period is about 200 ms to about 300 ms.

Figures 8A, 8B, 8C, 8D, 8E:
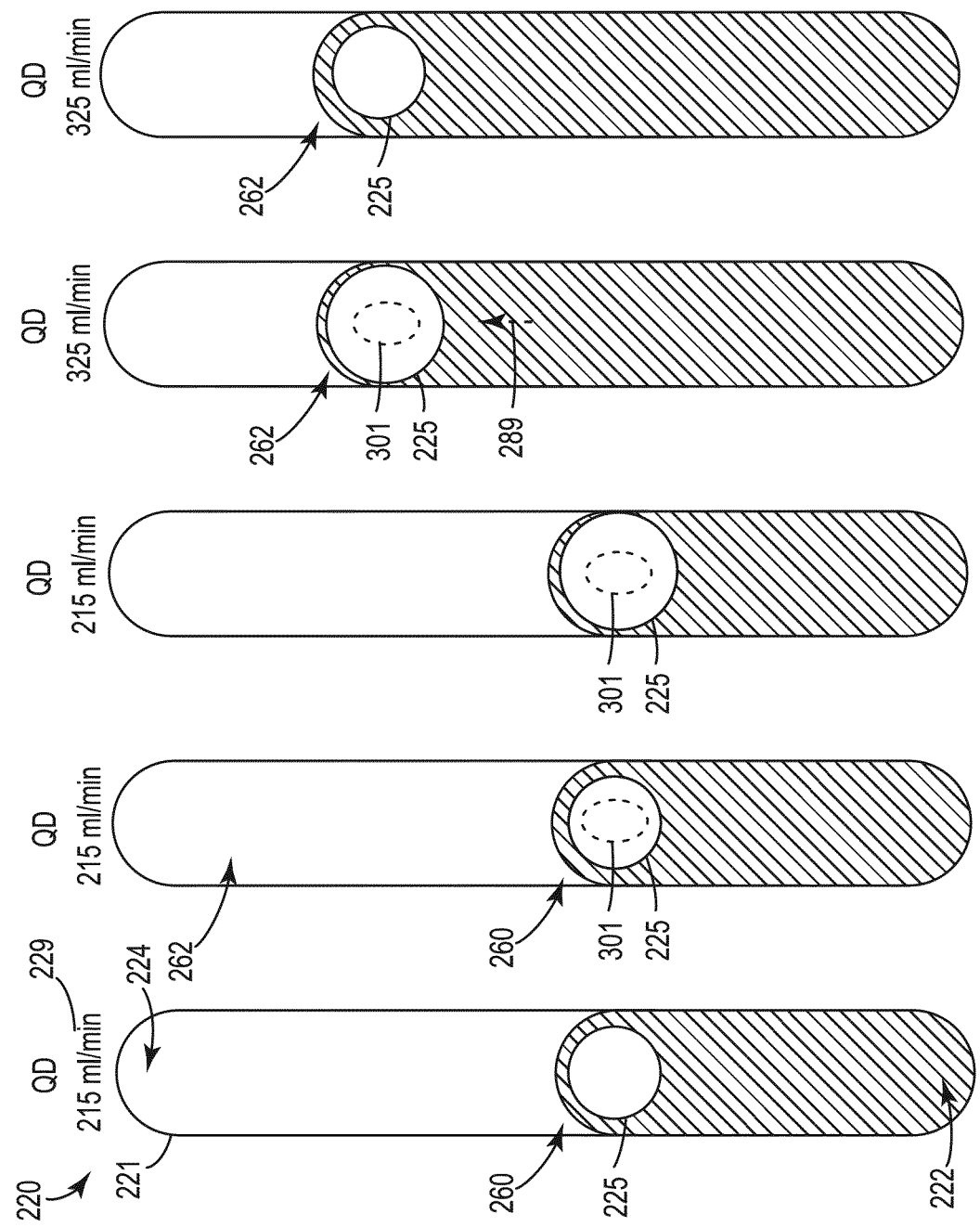

The indicator element 225 is configured in the locked state as shown in FIG. 8A. A user has selected and maintained selection (e.g., maintained contact with) the indicator element 225 in FIG. 8B as represented by the user selection representation 301. If the user maintains selection of the indicator element 225 for the entire unlock time period (e.g., until the expiration of the unlock time period), the indicator element 225 may become unlocked such that the user may move (e.g., drag) the indicator element 224 along the bar element 221 for parameter adjustment.

The exemplary systems and methods may further provide indications or notifications to a user representative of the unlock time period such that the user is aware of the unlock time period and the expiration of the unlocked time period. For instance, a notification may be provided to the user when the unlock time period expires. Such notification when the unlock time period expires may include one or more visual, auditory, and/or haptic notifications. For example, as shown in FIG. 8C, after a user has maintained selected (e.g., contact) with the indicator element 225 for the unlock time period, the indicator element 225 has become graphically emphasized. More specifically, the indicator element 225 in this embodiment has increased in graphical size (e.g., compare the indicator element 225 in FIG. 8B to the indicator element 225 in FIG. 8C). In other embodiments, the graphical emphasization may include shape changes, color changes, sounds, animations, vibrational or other haptic feedback, etc.

In response to the unlock time period expiring while the user has maintained selection of the indicator element 225, the user may move (e.g., drag) the indicator element 225 along the bar element 221 to adjust the associated parameter. As shown in FIG. 8D, a user has moved (as shown by arrow 289) the indicator element 225 towards the second end 224 to increase the parameter to 325 ml/min. After a user has selected the desired value for the parameter to be changed, or set to, the user may release, or unselect, the indicator element 225. As shown in FIG. 8E, a user has released the indicator element 225 at the position associated with the 325 ml/min value, which configures the indicator element 225 into the locked state.

To show that the indicator element 225 is configured into the locked state, a notification may be provided. For example, as shown, the indicator element 224 has been graphically de-emphasized. More specifically, the graphical size of the indicator element 225 has been decreased from the graphically-emphasized size while being adjusted to the original, or default, size when configured in the locked state.

Figure 9A:
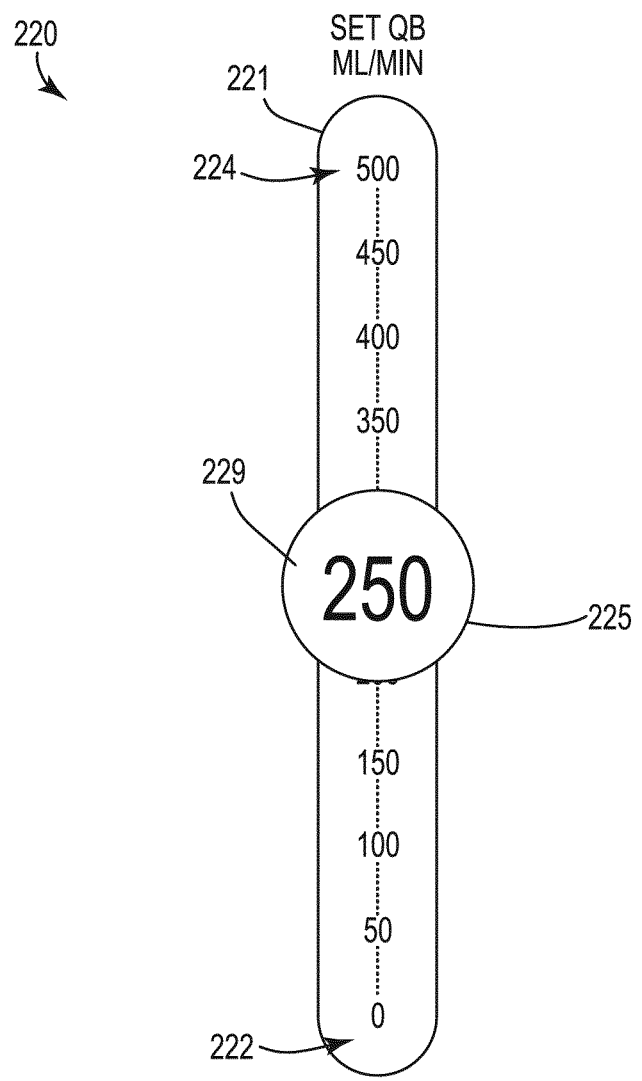
Figure 9B:
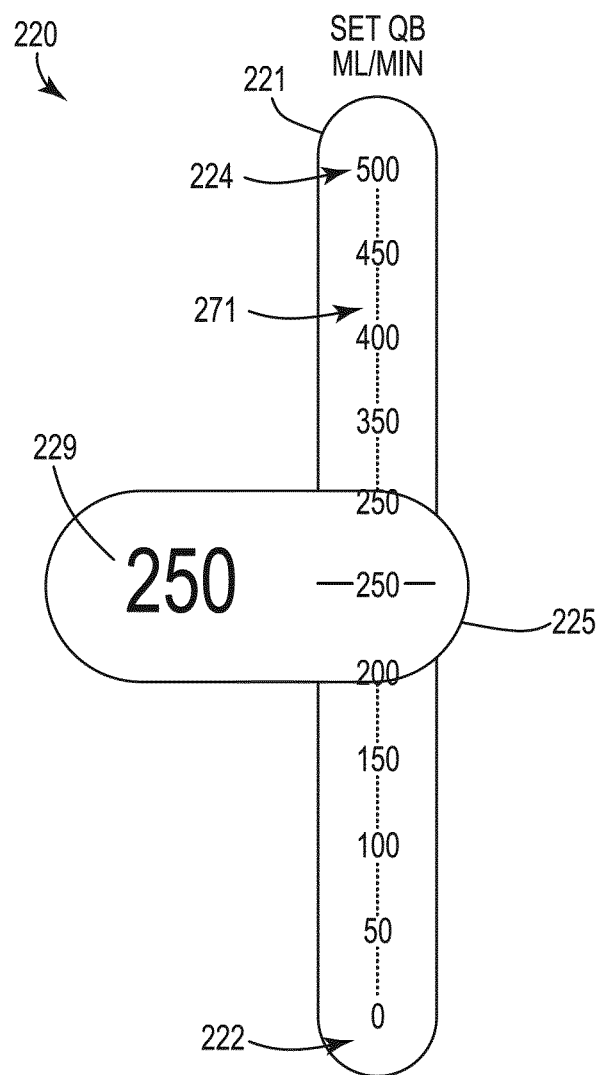
Figure 9C:
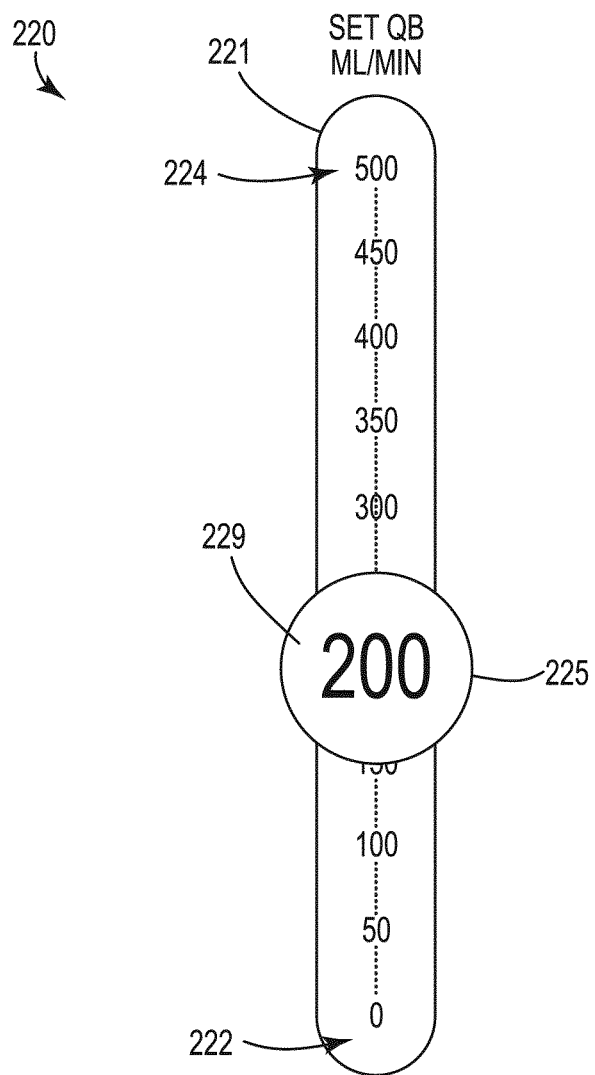

Another exemplary embodiment of a bar-type parameter adjustment element 220 is depicted in FIGS. 9A-9C. In this example, the bar-type parameter adjustment element 220 is configured to adjust the blood flow rate (QB), which may be displayed by itself in parameter adjustment region 210 of the graphical user interface 200.

In this embodiment, the bar element 221 may include a plurality of value indications, or "tick marks," 271 located along the bar element 221 to indicate to a user the various parameter values available for adjusting the associated parameter. Further, the indicator element 225 may further include the alphanumeric depiction 229 of present value of the associated parameter, which in this example, is 250 ml/min. More specifically, the alphanumeric depiction 229 is located within the graphical perimeter of indicator element 225.

When a user selects the indicator element 225 such as, e.g., using a finger touching the indicator element 225 on a touchscreen, the selection may obscure the alphanumeric depiction 229 of the present value of the associated parameter. In the embodiment depicted in FIGS. 9A-9C, when the indicator element 225 is selected and, e.g., unlocked by maintaining selection of the indicator element 225 for the unlock time period, the indicator element 225 may be graphically emphasized and the alphanumeric depiction 229 may be displayed away from the bar element 221 (e.g., to avoid being obscured by the user selection). More specifically, as shown in FIG. 9B, the indicator element 225 has changed into a capsule, or stadium, shape (e.g., a "pill-shape") in response to a user selecting and maintaining selection of the indicator element 225 for an unlock time period and the alphanumeric depiction 229 may move away from the bar element 221. More specifically, in this example, the alphanumeric depiction 229 has moved to the left of the bar element 221, e.g., so as to not be obscured by the user's selection (e.g., finger contacting the indicator element 225). A user may then move the indicator element 225 along the bar element 221 to adjust the associated element. As shown in FIG. 9C, a user has moved the indicator element 225 towards the first end 222 of the bar element 221 to decrease the associated parameter to 200 ml/min.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the systems and methods described herein. Various modifications of the illustrative embodiments, as well as additional embodiments of the disclosure, will be apparent upon reference to this description.

What is claimed is:

1. An extracorporeal blood treatment system comprising:
   extracorporeal blood treatment apparatus comprising one or more pumps, one or more sensors, and one or more disposable elements for use in performing an extracorporeal blood treatment;
   a display comprising a graphical user interface configured to depict a parameter adjustment region corresponding to a plurality of parameters related to the extracorporeal blood treatment performable using the extracorporeal blood treatment apparatus; and
   a processor operatively coupled to the extracorporeal blood treatment apparatus and the display and configured to:
      provide a plurality of parameters related to the extracorporeal blood treatment performable using the extracorporeal blood treatment apparatus and a plurality of reference values, each of the plurality of reference values is associated with a different parameter of the plurality of parameters, wherein each of the plurality of reference values represents a selected prescription value entered prior to an extracorporeal blood treatment and during setup of the extracorporeal blood treatment, a preset default value saved in the system, or a saved value from previous treatment or previous prescription data for a patient for each associated parameter of the plurality of parameters;
      display the parameter adjustment region on the graphical user interface, wherein the parameter adjustment region comprises a plurality of bar-type parameter adjustment elements displayed simultaneously, wherein each of the plurality of bar-type parameter adjustment elements is associated with and configured to adjust a different parameter of the plurality of parameters related to the extracorporeal blood treatment performable using the extracorporeal blood treatment apparatus, wherein each of the plurality of bar-type parameter adjustment elements comprises:
         a bar element extending from a first end representative of a lower value for the associated parameter to a second end representative of an upper value for the associated parameter and scaled such that a midpoint between the first end and the second end is representative of the reference value for the associated parameter, and an indicator element located along the bar element between the first end and the second end indicative of a present value of the associated parameter, wherein the plurality of bar-type parameter adjustment elements are aligned with respect to each other such the bar elements of the plurality of bar-type parameter adjustment elements are parallel each other; and change a parameter of the plurality of parameters related to the extracorporeal blood treatment performable using the extracorporeal blood treatment apparatus in response to a user using the bar-type parameter adjustment element associated with the parameter to adjust the parameter.

2. The system of claim 1, wherein changing a parameter of the plurality of parameters related to the extracorporeal blood treatment performable using the extracorporeal blood treatment apparatus in response to a user using the bar-type parameter adjustment element associated with the parameter to adjust the parameter comprises changing the parameter in response to a user tapping an area between the indicator element and the first end or an area between the indicator element and the second end along the bar element of the associated bar-type parameter adjustment element to decrease or increase, respectively, the parameter by a step percentage of the upper value for the parameter.

3. The system of claim 2, wherein the step percentage is less than or equal to about 10 percent of the upper value for the parameter.

4. The system of claim 1, wherein changing a parameter of the plurality of parameters related to the extracorporeal blood treatment performable using the extracorporeal blood treatment apparatus in response to a user using the bar-type parameter adjustment element associated with the parameter to adjust the parameter comprises changing the parameter in response to a user selecting the indicator element and dragging the indicator element along the bar element towards the first end or the second end of the associated bar-type parameter adjustment element to decrease or increase, respectively, the parameter.

5. The system of claim 4, wherein the processor is further configured to execute:

changing the parameter to a value associated with a new position of the indicator element along the bar element in response to the user maintaining selection of the indicator element at the new position for a confirmation time period.

6. The system of claim 1, wherein the indicator element is configurable in a locked state and in an unlocked state, wherein the indicator element is unmovable along the bar element by selecting and dragging the indicator element when in the locked state, wherein the indicator element is movable along the bar element by selecting and dragging the indicator element when in the unlocked state, wherein the processor is further configured to execute or the method further comprises:

configuring the indicator element in the locked state when the indicator element is not selected by a user, and configuring the indicator element in the unlocked state in response to a user selecting and maintaining selection of the indicator element for a unlock time period.

7. The system of claim 6, wherein the unlock time period is less than or equal to 250 milliseconds.

8. The system of claim 1, wherein each of the plurality of bar-type parameter adjustment elements further comprises an alphanumeric depiction of the associated parameter, wherein the processor is further configured to execute or the method further comprises:

initiating an adjustment of a parameter of the plurality of parameters in response to a user selecting the alphanumeric depiction of the bar-type parameter adjustment element of the plurality of bar-type parameter adjustment elements associated with the parameter, and displaying an alphanumeric parameter entry region in response to selection of the alphanumeric depiction to allow the user to change the associated parameter.

9. The system of claim 1, wherein the processor is further configured to execute:

displaying on the graphical user interface one or more blood process feature graphical regions corresponding to one or more processes of the extracorporeal blood treatment system, and display the parameter adjustment region in response to a user selecting a blood process feature graphical region of the one or more blood process feature graphical regions.

10. The system of claim 1, wherein the plurality of parameters are related to one of priming, ultrafiltration, and dialysis fluid.

11. The system of claim 1, wherein the display comprises a touchscreen.

12. A method for an extracorporeal blood treatment system comprising:

providing extracorporeal blood treatment apparatus comprising one or more pumps, one or more sensors, and one or more disposable elements for use in performing an extracorporeal blood treatment;

displaying a parameter adjustment region corresponding to a plurality of parameters related to the extracorporeal blood treatment performable using the extracorporeal blood treatment apparatus on a graphical user interface on a display;

providing a plurality of parameters related to the extracorporeal blood treatment performable using the extracorporeal blood treatment apparatus and a reference value for each parameter of the plurality of parameters, wherein the reference value represents a selected prescription value entered prior to an extracorporeal blood treatment and during setup of the extracorporeal blood treatment, a preset default value saved in the system, or a saved value from previous treatment or previous prescription data for a patient for each associated parameter of the plurality of parameters;

displaying the parameter adjustment region on the graphical user interface, wherein the parameter adjustment region comprises a plurality of bar-type parameter adjustment elements displayed simultaneously, wherein each of the plurality of bar-type parameter adjustment elements is associated with and configured to adjust a different parameter of the plurality of parameters related the extracorporeal blood treatment performable using the extracorporeal blood treatment apparatus, wherein each of the plurality of bar-type parameter adjustment elements comprises:

a bar element extending from a first end representative of a lower value for the associated parameter to a second end representative of an upper value for the associated parameter and scaled such that a midpoint between the first end and the second end is representative of the reference value for the associated parameter, and an indicator element located along the bar element between the first end and the second end indicative of a present value of the associated parameter, wherein the plurality of bar-type parameter adjustment elements are aligned with respect to each other such the bar elements of the plurality of bar-type parameter adjustment elements are parallel each other; and changing a parameter of the plurality of parameters related to the extracorporeal blood treatment performable using the extracorporeal blood treatment apparatus in response to a user using the bar-type parameter adjustment element associated with the parameter to adjust the parameter.

13. The method of claim 12, wherein changing a parameter of the plurality of parameters related to the extracorporeal blood treatment performable using the extracorporeal blood treatment apparatus in response to a user using the bar-type parameter adjustment element associated with the parameter to adjust the parameter comprises changing the parameter in response to a user tapping an area between the indicator element and the first end or an area between the indicator element and the second end along the bar element of the associated bar-type parameter adjustment element to decrease or increase, respectively, the parameter by a step percentage of the upper value for the parameter.

14. The method of claim 13, wherein the step percentage is less than or equal to about 10 percent of the upper value for the parameter.

15. The method of claim 12, wherein changing a parameter of the plurality of parameters related to the extracorporeal blood treatment performable using the extracorporeal blood treatment apparatus in response to a user using the bar-type parameter adjustment element associated with the parameter to adjust the parameter comprises changing the parameter in response to a user selecting the indicator element and dragging the indicator element along the bar element towards the first end or the second end of the associated bar-type parameter adjustment element to decrease or increase, respectively, the parameter.

16. The method of claim 15, wherein the processor is further configured to execute or the method further comprises:

changing the parameter to a value associated with a new position of the indicator element along the bar element in response to the user maintaining selection of the indicator element at the new position for a confirmation time period.

17. The method of claim 12, wherein the indicator element is configurable in a locked state and in an unlocked state, wherein the indicator element is unmovable along the bar element by selecting and dragging the indicator element when in the locked state, wherein the indicator element is movable along the bar element by selecting and dragging the indicator element when in the unlocked state, wherein the processor is further configured to execute or the method further comprises:

configuring the indicator element in the locked state when the indicator element is not selected by a user, and configuring the indicator element in the unlocked state in response to a user selecting and maintaining selection of the indicator element for a unlock time period.

18. The method of claim 17, wherein the unlock time period is less than or equal to 250 milliseconds.

19. The method of claim 12, wherein each of the plurality of bar-type parameter adjustment elements further comprises an alphanumeric depiction of the associated parameter, wherein the processor is further configured to execute or the method further comprises:

initiating an adjustment of a parameter of the plurality of parameters in response to a user selecting the alphanumeric depiction of the bar-type parameter adjustment element of the plurality of bar-type parameter adjustment elements associated with the parameter, and displaying an alphanumeric parameter entry region in response to selection of the alphanumeric depiction to allow the user to change the associated parameter.

20. The method of claim 12, wherein the processor is further configured to execute or the method further comprises:

displaying on the graphical user interface one or more blood process feature graphical regions corresponding to one or more processes of the extracorporeal blood treatment system, and display the parameter adjustment region in response to a user selecting a blood process feature graphical region of the one or more blood process feature graphical regions.

21. The method of claim 12, wherein the plurality of parameters are related to one of priming, ultrafiltration, and dialysis fluid.

22. The method of claim 12, wherein the display comprises a touchscreen.

* * * * *